United States Patent [19]
Feaster

[11] Patent Number: 5,098,444
[45] Date of Patent: Mar. 24, 1992

[54] EPIPHAKIC INTRAOCULAR LENS AND PROCESS OF IMPLANTATION

[76] Inventor: Fred T. Feaster, 1125 College Ave., Fort Worth, Tex. 76104

[21] Appl. No.: 494,762

[22] Filed: Mar. 16, 1990

[51] Int. Cl.$^5$ .............................................. A61F 2/16
[52] U.S. Cl. ................................................. 623/6
[58] Field of Search ........................................ 623/6

[56] References Cited

U.S. PATENT DOCUMENTS

| 4,573,998 | 3/1986 | Mazzocco | 623/6 |
| 4,585,456 | 4/1986 | Blackmore | 623/6 |

FOREIGN PATENT DOCUMENTS

0234365A1  4/1986  German Democratic Rep. .... 623/6

Primary Examiner—Ronald Frinks
Attorney, Agent, or Firm—Arthur F. Zobal

[57] ABSTRACT

In one implantation process, the intraocular lens implant is placed partially or completely on the anterior capsular surface of the human crystalline lens and is attached thereto by means of glue or adhesive. The implant has overall edge-to-edge dimensions such that it does not extend beyond the periphery of the human lens. In several embodiments, adhesive receiving wells are formed in the implant lens near the periphery to facilitate attachment of the implant lens to the human lens. In another embodiment, the implant lens has structure extending from its posterior side for engaging the human lens to space the implant lens from the human lens. In still another embodiment the posterior side of the implant lens is vaulted such that the central portion of the implant lens does not engage the human lens.

In another implantation process, the intraocular lens is attached to a previously implanted intraocular lens for optical correction purposes. Attachment may be with adhesives or mechanical means such as clips.

25 Claims, 11 Drawing Sheets

EPIPHAKIC INTRAOCULAR LENS AND PROCESS OF IMPLANTATION

BACKGROUND OF THE INVENTION

1. Field of the Invention

The invention relates to artificial intraocular lens implants for the phakic or pseudophakic human eye.

2. Description of the Prior Art

It is well known that there are many ways the human eye can deviate from the optical ideal of emmetropia, in which images are precisely focused on the retina naturally, without assistance or effort, resulting in clear vision requiring no additional optical correction. Such deviations from the optical ideal of emmetropia which produce an optically non-ideal situation, or ammetropia, include:

1. Myopia (near-sightedness)—in which the image of the object of regard is focused in front of the retina producing a blurry image on the retina itself.
2. Hyperopia (far-sightedness)—in which the image of the object of regard is focused behind the retina producing a blurry image on the retina itself.
3. Astigmatism (asymmetry or irregularity of corneal curvature)—producing an irregular and therefore blurry image.
4. Presbyopia—loss of the accommodative ability of the naturally occurring human crystalline lens, making near objects blurry.
5. A combination of the above.

The presence of these optically aberrant or ammetropic conditions is due to a relative mismatching of the optical powers of the optical elements of the eye (primarily the cornea and lens) with respect to the position of the retina, which produces a failure of the eye as an optical system to function in the desired manner to give clear vision. This can occur in spite of the otherwise normal condition of the tissues of the optical elements involved.

Many methods have been developed in an attempt to correct the above mentioned group of naturally occurring ammetropic conditions of myopia, hyperopia, astigmatism, and presbyopia including:

1. Spectacle correction—in which refracting lenses in glasses frames are positioned in front of the eye, external to, and not in contact with the cornea.
2. Contact lenses—which physically rest upon the external surface of the cornea and its tear film and alter the overall optical status of the eye by means of their refractive optical power and also by the physical presence on the corneal surface thereby neutralizing irregularities of the corneal surface. A technique known as orthokeratology has been developed in which the shape of the cornea is modified by fitting a contact lens having a particular desired curvature which is intended to change the shape of the cornea to the curvature of the contact lens. This technique has had minimal success due to the nonpermanent nature of the induced curvature change on the cornea by the contact lens, and is practiced little today.
3. Refractive surgery—in which the optical refractive status of the eye is altered through some surgical procedure. One general group of procedures is referred to as corneal refractive surgery in which a change in the corneal shape, or refractive index, or both, is surgically induced, thereby changing the corneal optical power. Examples of corneal refractive surgery are:

A. Radial keratotomy—(developed initially by Sato in Japan in 1939 and more recently popularized by S.N. Fyodorov in Russia and brought to the U.S. by Bores) in which radial incisions are made into the substance of the corneal tissue changing its shape. This procedure, along with many variations in the orientation, length, number and depth of incisions, has been used to correct myopia, astigmatism, and more recently hyperopia.

B. Keratophakia (originated by Jose Barraquer—Bogota, Colombia) and its variations such as epikeratoplasty (developed by Kaufman and MacDonald) —in which properly preshaped human donor tissue is surgically placed on the external surface of the cornea, thereby altering the overall corneal shape and consequently its refractive effect.

C. Keratomileusis—(originated by Barraquer, Colombia)—in which the patient's surface corneal tissue is removed, reshaped in some fashion at surgery, and replaced on the corneal surface in its new configuration.

D. Synthetic corneal onlay—in which a synthetic material (silicone or hydrogel-like material) is placed directly onto the corneal surface, thereby altering the corneal shape.

E. Synthetic corneal inlay—(developed by Peter Choyce)—in which a pocket is surgically developed within the layers of the corneal tissue into which is slid or placed a polysulfone disc which, by its higher refractive index than the surrounding normal corneal tissue, alters the overall optical power of the cornea. Note U.S. Pat. No. 4,624,669. Another type of corneal inlay procedure is also under development notably by Dr. Theodore Werblin in which the surface corneal tissue is removed centrally and a refractive disc (which is made of synthetic silicone-like or hydrogel-like materials)is placed within this bed, after which the previously removed corneal tissue is replaced over the inlay. The inlay is consequently "sandwiched" between the previously removed anterior corneal surface tissue in front and the posterior corneal tissue behind, and has its effect, unlike the inlay of Choyce, primarily by means of changing the corneal curvature.

F. Corneal laser sculpting—in which by means of the application of laser energy (notably currently eximer laser energy) to the corneal tissue, the cornea is reconfigured by means of incisions (as in radial keratotomy) or reshaped (sculpted) to alter its configuration.

Another general type of refractive surgery has been directed toward altering the length of the eye by means of scleral resection or support, generally intending to shorten the anterior/posterior ocular length in long, highly myopic eyes. This surgery is extremely complex, dangerous, and generally ineffective and has fallen into disuse.

A different surgical approach in highly myopic eyes has been recently advocated by Verzella in which the clear (noncataractous) lens is removed, leaving the eye aphakic. Because of the loss of the optical converging power of the naturally occurring human lens, the eye is rendered less myopic. Some have advocated the removal of the natural lens and replacement with an intraocular lens of less convergent power, which also makes the eye less myopic.

Cataract removal, particularly with the advent of intraocular lenses, must technically also be considered a type of refractive surgery. However, it differs considerably from the previously described procedures in that the eye, specifically the optical element—the human lens, is not normal, but is cataractous. The eye may in fact be otherwise emmetropic. The cataract surgery is performed expressly for the purpose of removal of the cataract for vision improvement. The intraocular lens is implanted for optical correction of the eye which now requires optical correction only because the cataractous lens has now been removed.

Also, technically, the surgery of keratoprosthesis implantation is a refractive procedure in which an optical element with a surrounding stabilizing element is implanted (imbedded actually) in the tissue of the cornea into which it finally becomes an integral part. This procedure, however, is reserved for the most desperate of situations in which usually the corneal tissue is markedly scarred and opaque and there is little if any hope of successful visual rehabilitation with any other surgical approach.

Another surgical procedure for altering the refractive status of the ammetropic usually myopic but otherwise healthy, phakic eye has been the implantation of an intraocular lens within the phakic eye, virtually exclusively in the anterior chamber. This particular location has been used in order to avoid physical contact between the intraocular lens and the normal human lens which might result in traumatic damage to the human lens and possibly cataract formation. In the late 1940's and early 1950's, when this type of procedure was first attempted, complications from these anterior chamber implants such as chronic inflammation within the eye (iritis), corneal swelling and cloudiness, glaucoma, and cataracts did indeed occur. These complications were the result both of poor intraocular lens designs (which resulted in implant being too close to the cornea, particularly peripherally, and to the human lens centrally), materials and manufacture. The complication rates of these early anterior chamber implant procedures were so high and the results were so poor that the procedure was abandoned.

With our improved understanding of intraocular lens biopathology, lens designs, materials and manufacturing techniques, the procedure of anterior chamber intraocular lens implantation in phakic eyes has recently been resurrected with modern anterior chamber intraocular lens implants. These phakic implants have been implanted virtually exclusively in the anterior chamber to avoid the previously mentioned complications of iritis, corneal swelling and decompensation, glaucoma, and especially cataract, all of which as mentioned, have been encountered before. The anterior chamber is the location which affords the greatest separation between the implanted intraocular lens and the human lens. This principle of maximum separation between the intraocular lens implant and the human lens has been reinforced by the recent development of anterior chamber implants for refractive correction of phakic eyes which have a greater anterior vault or angulation than anterior chamber implants used for cataract surgery. This greater angulation, however, has the considerable disadvantage of placing the implant closer to the cornea risking corneal touch with resultant damage, eventual swelling and decompensation.

A final method of refractive correction in the phakic eye has been described by Mazzocco (U.S. Pat. No. 4,573,998) Blackmore (U.S. Pat. No. 4,585,456), and Kelman (U.S. Pat. No. 4,769,035) in which it is proposed that the optically corrective device be placed directly on the crystalline lens of the eye. This general concept of placement of the optical device directly upon the crystalline lens places the implant as far as possible from the delicate structures of the cornea, specifically the endothelium, which is a distinct advantage over phakic implants placed in the anterior chamber. The particular design of Mazzocco specifically addresses a method of implantation comprising a series of steps including an intraocular lens having a deformable optical portion which must be compressed to about 80% or more of the cross-sectional diameter prior to insertion into the eye. The compressible implant is described as having various mechanisms of fixation, which include: 1. Suturing to the iris anteriorly by means of a suture passed through the iris and through openings located in the periphery of the implant device (FIGS. 9, 10, 21, 21a, 22, 22a in the Mazzocco U.S. Pat. No. 4,573,998), or 2. By means of peripheral fixating members which hold the implant in position through physical contact and pressure upon the tissues of the periphery of the eye, either in the anterior chamber in the angle (FIGS. 11, 12, 15-20, 23,24, 25, 26 in the Mazzocco U.S. Pat. No. 4,573,998), or more pertinent to the discussion here, in the posterior chamber, peripheral to the lens and posterior to the iris in the ciliary sulcus (FIG. 60 in Mazzocco patent). Therefore, although the proposed optically corrective implant devices of Mazzocco are proposed to lie upon the human crystalline lens, they obtain their fixation from a location other than the human crystalline lens, namely the angle (anterior chamber), iris, or the ciliary sulcus (posterior chamber). Note also Blackmore (U.S. Pat. No. 4,585,466) and Kelman (U.S. Pat. No. 4,769,035).

To summarize, the corneal refractive procedures are;
1. Incisional reshaping (surgical knife or laser)—such as radial keratotomy.
2. Corneal onlays.
   A. Human donor tissue—keratophakia, epikereatoplasty.
   B. Reshaped patient's tissue—keratomileusis.
   C. Synthetic material.
3. Corneal inlays.
   A. Polysulfone—refractive index change effect.
   B. Silicone or hydrogel—configuration change effect (mainly).
4. Laser corneal reshaping.
5. Keratoprosthesis implantation.
6. Scleral resection—no longer widely used.
7. Lensectomy
   A. Clear lensectomy (either alone or with implantation of a low power IOL)
   B. Cataract extraction with IOL implantation.
8. Phakic IOL implantation—uses anterior chamber IOL (modified with greater anterior vault)
9. IOL placed on the anterior surface of the iris or anterior surface of the lens and held in position by peripheral fixation members.

With particular reference to the compressible IOL described by Mazzocco, it should be noted that the various mechanisms of fixation he proposes for stabilization of the implant (anterior chamber angle, iris and ciliary sulcus) are well known to be less biocompatible (and therefore less acceptable) when they have been utilized for fixation of intraocular lenses which have been implanted after cataract extraction. It is reasonable for anyone skilled in the art to deduct from this previous clinical experience with intraocular lenses implanted after cataract extraction, that these mechanisms of fixation would be similarly less biocompatible and therefore less desirable in any intraocular lens implant device placed within the eye directly upon the crystalline lens.

This is a particular concern since it is anticipated that surgical optical refractive correction would be attempted in a patient population generally considerably younger than the population in which cataract extraction is common. Therefore, it would be expected that a younger patient would require a longer lifetime of intraocular acceptance from such an implant. This increased lifetime expectancy puts an even greater demand on any phakic implant design to be maximally biocompatible, and a crucial feature of any phakic implant design is its fixation mechanism. A maximally biocompatible fixation mechanism is essential to ensure long-term ocular acceptance of any phakic implant. Clearly, the more rigorous design requirements of a phakic implant eliminate the previously proposed fixation mechanisms of Mazzocco, Blackmore, and Kelman of anterior chamber angle, iris, or ciliary sulcus fixation as acceptable options. Unfortunately, the fixation mechanism which has been found to be most biocompatible for intraocular lenses implanted after cataract extraction, namely, fixation within the capsular bag, is not available for phakic implant fixation since the human crystalline lens remains intact.

This overall situation, therefore, leaves the questions of a suitably biocompatible fixation mechanism for a phakic implant which physically rests partially or completely on the human crystalline lens unanswered by the prior art.

SUMMARY OF THE INVENTION

It is an object of the invention to provide a fixation process for a phakic implant which physically rests partially or completely on the anterior (capsular) surface of the natural human lens (hereinafter referred to as an epiphakic implant) wherein the epiphakic implant is fixated directly to the anterior capsular surface of the human lens.

It is another object of the invention to provide an epiphakic intraocular lens implant structured such that it may be fixated directly to the anterior capsular surface of the human lens.

It is a further object of the invention to provide an intraocular lens implant for refractive correction of the phakic eye that is placed partially or completely on the anterior capsular surface of the human crystalline lens (epilentricular implant) and is attached thereto by means of gluing or adhesion. The implant device has overall edge-to-edge dimensions such that the implant does not overlap, or overlaps only minimally, the zonular attachments to the human lens. The edge periphery has optimally thin, smooth and posteriorly located edges to minimize mechanical contact and damage to the adjacent iris.

Rather than depending on angle, iris or ciliary sulcus fixation, the epiphakic intraocular lens implant is fixated by "gluing" (or making otherwise adherent) the implant directly to the anterior capsular surface of the lens. This mechanism of fixation has the advantage of relying on the relatively nonreactive and durable anterior capsule of the human crystalline lens, thereby avoiding contact with the more delicate, reactive and less tolerant tissues of the angle of the anterior chamber, the iris, or ciliary sulcus. Eliminating the need for contact with these structures for fixation represents a superior and more biocompatible fixation mechanism.

In several embodiments, adhesive receiving "wells" or receptacle sites are formed in the implant lens near the periphery to facilitate attachment of the implant lens to the human lens. In another embodiment, the implant lens has structures extending from its posterior side or surface for engaging the human lens to space the implant lens from the human lens. In still another embodiment the posterior side of the implant lens is vaulted such that the central portion of the implant lens does not engage the human lens.

The above process also has application in altering or correcting the optical power of an artificial intraocular lens previously implanted in the eye after removal of the human (usually cataractous) lens. In some cases, optical alteration or correction of the previously implanted artificial lens is necessary and desirable, however, surgical removal of the already implanted lens may be technically difficult and dangerous and correction cannot be made by removal and replacement of the previously implanted artificial intraocular lens.

Accordingly it is an object of the invention to attach a second artificial intraocular lens to the first implanted artificial intraocular lens for optical correction purposes. Attachment can be made with adhesive or with mechanical means.

The second artificial intraocular lens may have adhesive receiving "wells" or receptacle sites near its periphery or peripheral clips for attaching the second artificial intraocular lens to the first intraocular lens.

BRIEF DESCRIPTION OF THE DRAWINGS

In FIGS. 24–31 the haptics of the previously implanted artificial intraocular lens are not shown for purposes of clarity.

DETAILED DESCRIPTION OF THE PREFERRED EMBODIMENTS

Figures 1, 4:
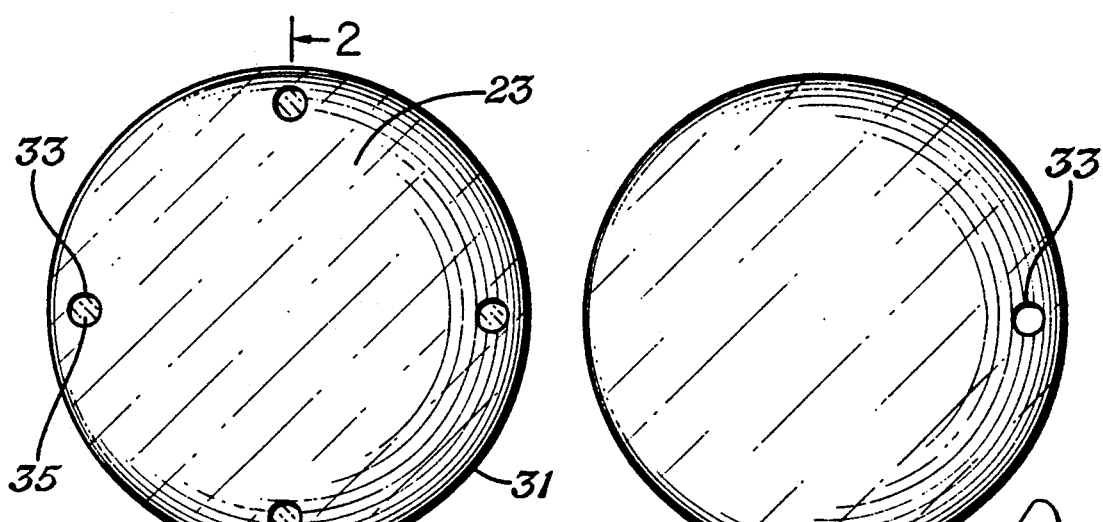
FIG. 1 is a plan view of an intraocular lens of one embodiment of the invention showing its anterior side.
FIG. 4 is a plan view of an intraocular lens of another embodiment of the invention showing its anterior side.
Figure 2:
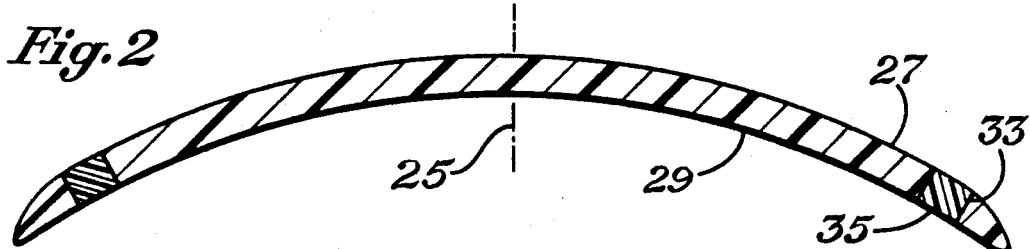
FIG. 2 is an enlarged cross-sectional view of FIG. 1, taken along the lines 2—2 thereof.
Figure 9:
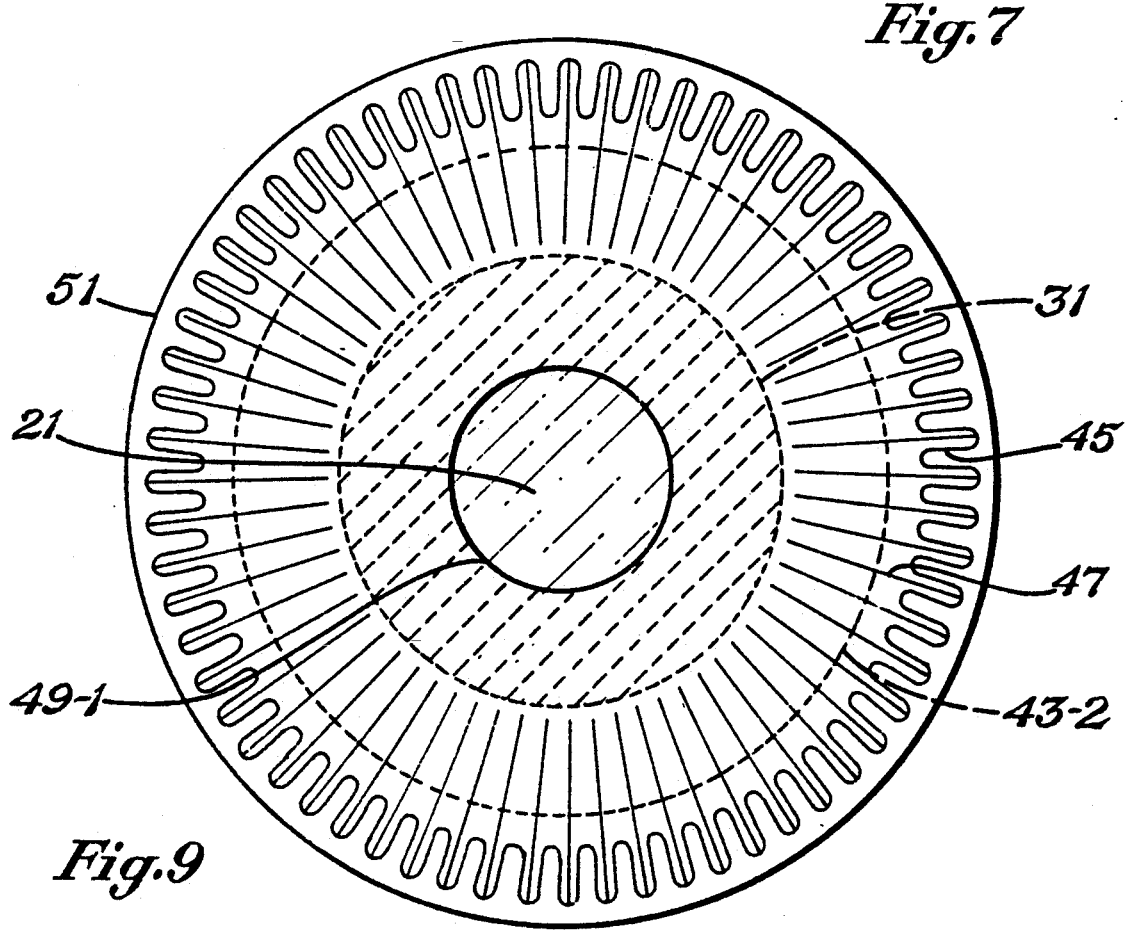
FIG. 9 is a front view of the human eye with the lens of the invention on the anterior surface of the human eye.
Figure 8:
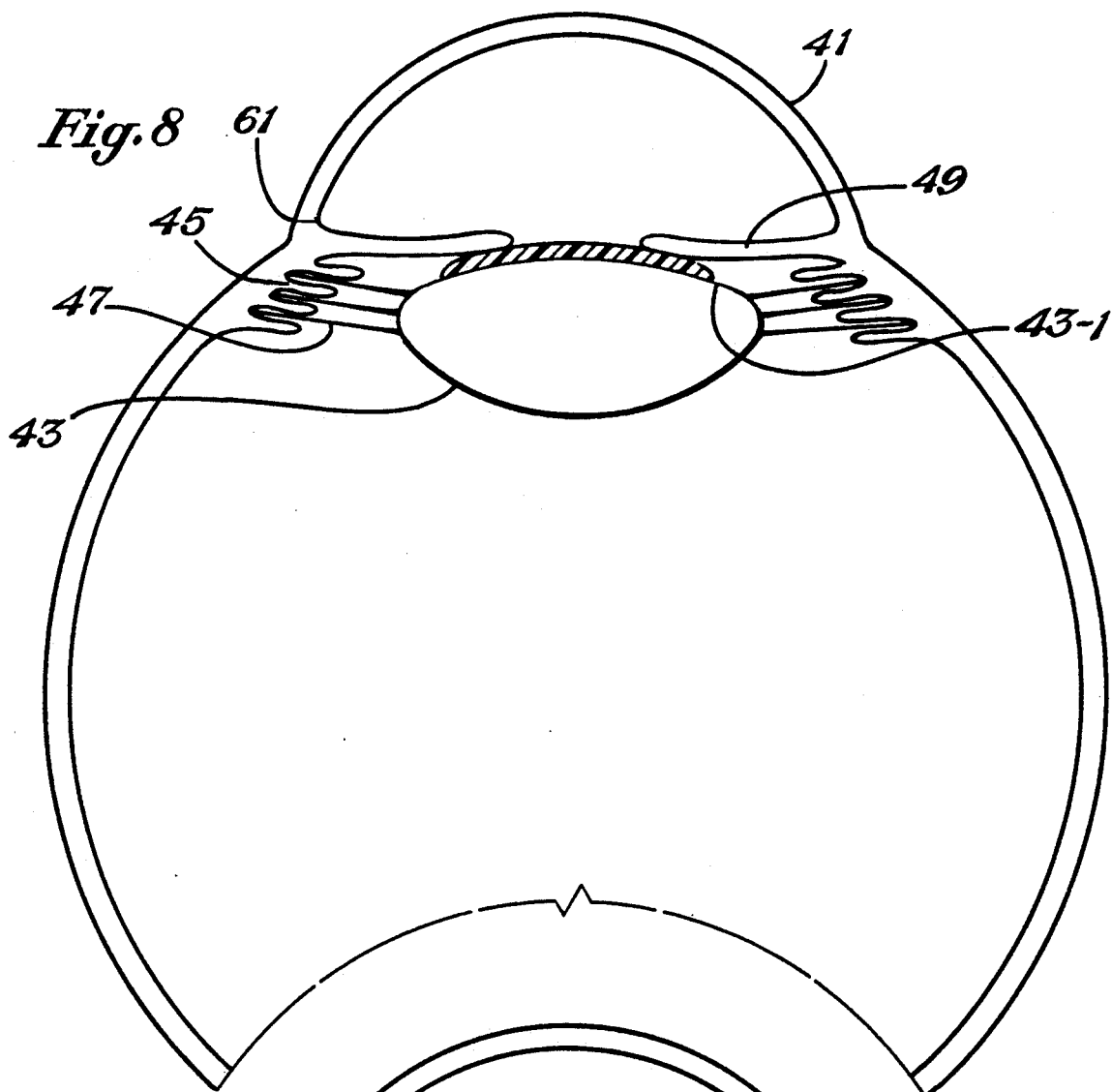
FIG. 8 is a cross-sectional view of the human eye showing one of the lenses of FIGS. 1-6 with its posterior side seated and "glued" against the anterior surface of the natural lens of the human eye. In this view the openings, wells, or channel of the artificial lens are not shown.

Referring now to FIGS. 1 and 2, the artificial intraocular lens shown is identified by reference numeral 21 and comprises a transparent optical member 23 having an optical axis 25 and anterior and posterior sides 27 and 29 respectively transverse to the optical axis and extending outward from the optical axis to a peripheral edge 31. Preferably the lens is circular in shape when seen in a plan view although it could be elliptical, triangular, square, or have other shapes as desired. Formed through the lens 21 near the peripheral edge 31 are four wells or openings or receptacle sites 33 which extend between sides 27 and 29. Located in the wells 33 is an energy labile (such as thermolabile) adhesive 35. The posterior side 29 of the lens may be shaped to conform to the anterior surface 43-1 of the human lens as shown in FIG. 8 although alternately the posterior side 29 may be shaped as described in conjunction with FIGS. 17–19 as will be described subsequently. In FIG. 8, reference numerals 41 identify the cornea; 43 the human lens; 45 the ciliary process; and 47 the zonule and 49 the iris. For maximal biocompatibility, the maximal overall edge-to-edge dimension (diameter when the implant lens is completely circular) should be sufficiently small so that the peripheral edges of the implant lens extend minimally, if at all, onto the zonular attachments to the anterior lens capsule peripherally. This is important so that the implant lens remains in position on the anterior surface of the human crystalline lens central to the central most portion of the zonular attachments to the lens capsule, thereby avoiding possible damage to the zonules which might result in zonular breakage and eventual dislocation of the human crystalline lens. The size of the implant lens 21 is chosen not only to remain central to the zonules but to remain larger than the pupillary space under usual conditions of bright and dim illumination (for most patients). It is anticipated this would require overall edge-to-edge dimensions to be no greater than approximately 5 to 6 mm but possibly as high as 6.5 to 7.0 mm. In FIG. 9, reference numerals 43-2 represents the margin of the human lens (peripheral edge); 45 the ciliary processes; 47 the zonules extending from the ciliary body to the anterior surface of the human lens; 31 the peripheral edge of the implant lens; 49-1 the pupillary margin (central edge of the iris; and 51 the limbus. In FIG. 9, the central iris border is represented at 49-1 but the remainder of the peripheral iris is treated as transparent in order to demonstrate the anatomical structures behind the iris, namely: the implant lens 21, the human lens, the ciliary processes, and the zonules.

In order to employ a lens 21 of the proper shape and dimensions, pre-measurements will be made of the human lens to determine the maximum dimensions of the implant lens 21 and the curvature of the posterior side 29 of the implant.

In the implantation process, an incision 61 (FIG. 8) is made through the limbus 51 of the eye of a sufficient size such that the implant lens 21 may be inserted through the incision into the eye with the posterior side 29 of the lens 21 seated against the anterior surface 43-1 of the human lens in optical alignment with the human lens and with the lens implant located centrally to the central most portion of the zonular attachments to the human lens capsule. The glue or adhesive 35 in the "wells" 33 is then subjected to a source of energy such as a laser beam from an argon laser, thereby altering the thermolabile glue material causing it to adhere and to adhere the implant lens to the underlying human lens capsule. This will represent a very localized reaction with virtually no significant damage to the underlying human lens tissue. The wells containing the glue 35 may be present in various locations and configurations as is determined optimal for complete and satisfactory fixation of the implant lens 21 to the human lens wherein the implant lens is rendered completely immobile.

Figure 3:
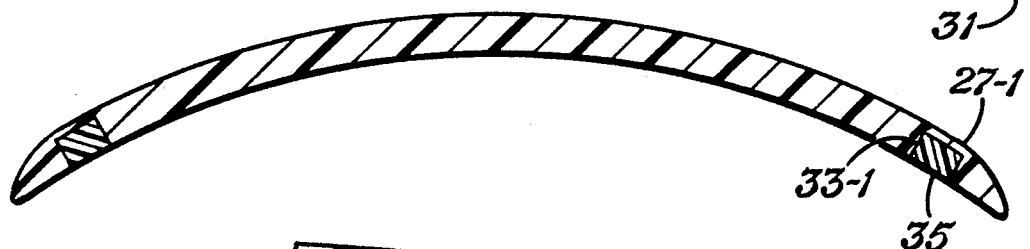
FIG. 3 is an enlarged cross-sectional view of the lens of FIG. 1 showing a modification thereof.

In FIG. 3 the lens 21 of FIGS. 1 and 2 has been modified in that the openings or wells 33-1 do not extend completely through the lens but have a thin covering or wall 27-1 on the anterior side to prevent exposure of the glue or adhesive 35 to the iris. In the embodiment of FIG. 3, the openings or wells 33-1 extend from the posterior side of the lens 21 to the wall 27-1. In this embodiment a laser or other energy source also will be employed to cause the glue to adhere and to attach the implant lens to the underlying human lens capsule. As an alternative, the "wells" 33-1 may have a thin wall on the posterior side of the lens 21. The "wells" 33-1 are filled with adhesive 35 from the anterior side and the posterior thin walls are energy labile whereby a laser beam may form openings through the posterior thin walls and adhere the adhesive 35 to the lens 21 and to the human lens capsule.

Figure 5:
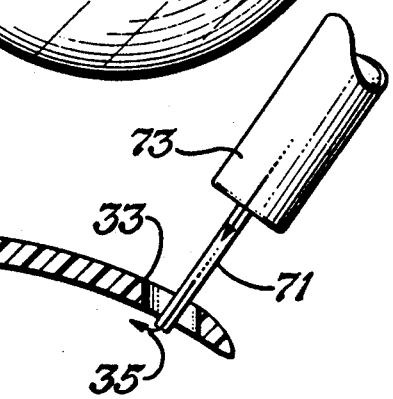
FIG. 5 is a cross-sectional view of the lens of FIG. 4 showing the injection of a glue or adhesive through the opening to the posterior side thereof.

In the embodiment of FIGS. 4 and 5, the lens 21 has a single opening 33 extending therethrough between sides 27 and 29. The opening has no glue or adhesive therein and after the lens 21 is inserted into the eye through the incision 61, and centered on the anterior surface or the human lens the glue or adhesive 35 in a fluid stare is injected to the posterior surface of the lens by way of a small tubular needle 71, of an injection means 73, inserted through the opening 33. The lens 21 then is compressed against the anterior capsular surface of the human lens.

Figure 6:
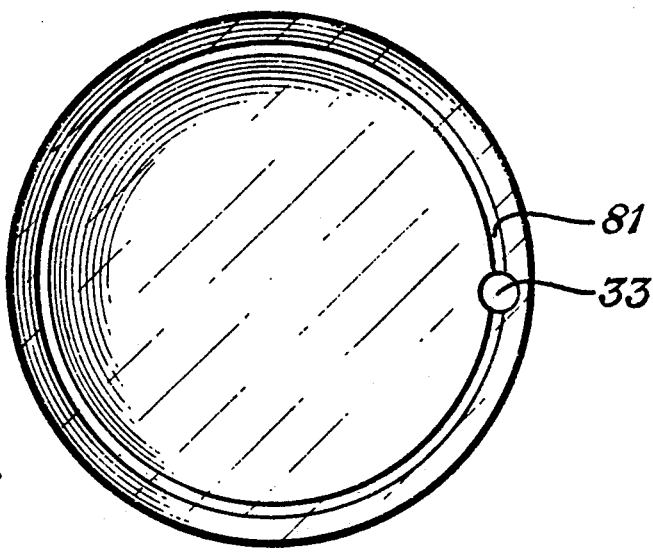
FIG. 6 is a plan view of an intraocular lens of another embodiment of the invention showing its posterior side.
Figure 7:
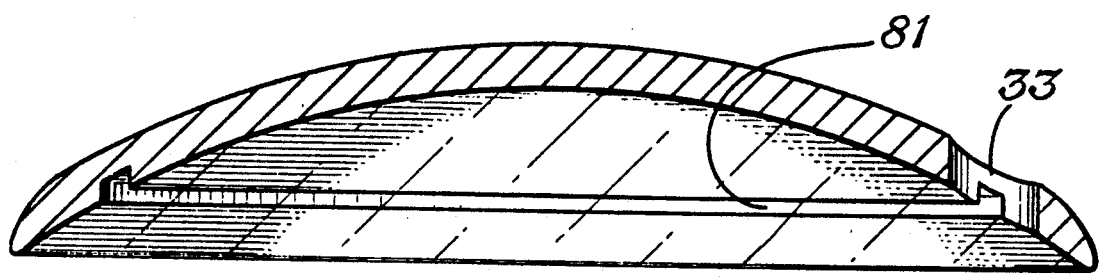
FIG. 7 is an enlarged cross-sectional view of the lens of FIG. 6.

In the embodiment of FIG. 6 and 7 the lens 21 has a single opening 33 extending therethrough between sides 27 and 29 leading to a circular channel 81 formed in its posterior side and employed to guide or direct the adhesive material 35 in a fluid state to its optimal location for fixation. In this embodiment the lens 21 may be inserted through the incision 61 and its posterior side 29 seated against the anterior surface of the human lens and the glue or adhesive in a fluid state injected with the device 71, 73 into the opening 33 for flow by way of the channel 81 for attaching the posterior side 29 of the lens 21 to the anterior surface of the human lens. The channel may not be completely circumferential.

In one embodiment the intraocular lens 21 may be formed of a relatively rigid plastic material such as polymethylmethacrylate (PMMA) to obtain a thinner lens although it could be formed of a flexible plastic material as disclosed in U.S. Pat. No. 4,573,998. The glue or adhesive 35 employed must meet with the necessary and acceptable standards for adequate permanent bonding with intraocular biocompatibility and may be a cyanoacrylate glue or suitable silicone adhesive for a lens 21 formed of PMMA. When a laser beam is employed to adhere the glue or adhesive to the human lens, the glue or adhesive will be a thermoplastic or thermosetting material.

There has been clinical experience in gluing contact lenses to the anterior corneal surface with reports of success up to five years duration. However, many attempts of gluing contacts met with only limited and temporary success due to undermining of the glued contact by the surrounding corneal epithelium which then eventually sheds (desquamates) along with the overlying contact causing the previously glued contact to become nonadherent. However, it should be noted that gluing as a permanent fixation mechanism for an epiphakic implant is expected to be entirely acceptable since the anterior surface of the lens is an anatomically smooth, continuous capsule composed of a stable basement membrane devoid of replicating cells, virtually nonmoving (except for the central change in radius of curvature associated with accommodation), and relatively nonreactive with a low metabolism and little turn over of biological components. The anterior lens capsule represents and ideal biologic surface for adherence and fixation to an epiphakic implant.

The procedure for implantation of the epiphakic intraocular lens is a microsurgical procedure requiring the use of an operating microscope. Anesthesia suitable for this procedure may be either general endotracheal anesthesia or local anesthesia (such as retrobulbar or periocular local anesthetic injection) which are commonly used for other routine types of intraocular surgery, such as cataract extraction. Similarly, the sterile technique and surgical principles involved are those customarily used routinely for intraocular surgery such as cataract extraction.

Preoperative pupillary dilation is necessary and can be accomplished with several topical mydriatic ophthalmic medications, such as Mydriacyl 1%, Cyclogyl or Neosynephrine 10%. A typical preoperative regimen consists of one drop of Cyclogyl 1% and one drop of Neosynephrine 10%, each medication being instilled in the operative eye a total of three times, the instillations being separated by about five minutes. The instillations should be completed approximately one half hour prior to surgery.

After preoperative dilation has been accomplished, the patient is positioned under the operating microscope, and the eyelids separated with an eyelid speculum. An incision through the surgical limbus, similar to that performed in cataract surgery, will provide a suitable entrance into the anterior chamber of the eye to allow for insertion of the implant into the eye. The usual location for the incision is in the 12 o'clock position, but other limbal locations may be selected for any particular case, depending on the individual measurements and anatomy of the specific patient under consideration. A fornix-based conjunctival flap is made to expose the underlying limbus in preparation for the limbal incision, and the limbal area is cleaned and hemostasis is achieved. A usual cataract type of multi-planed limbal incision (commonly a biplaned incision) is made at the surgical limbus. An initial partial thickness corneoscleral incision is made with a scalpel, after which the anterior chamber is entered through the partial thickness incision with a scalpel, and the incision completed with corneo-scleral scissors. The length of the incision is determined by the overall size of the implant lens. Should the implant be of a rigid or semi-flexible material, it is anticipated that an approximately 7 mm. incision will adequately allow passage and implantation of the implant lens (whose overall dimension is anticipated to be approximately 6 mm.). Should the implant be compressible or foldable, it is anticipated that a considerable smaller incision size might be acceptable, possibly as small as 2 to 3 mm. in length. Standard instruments such as tissue forceps will serve suitably to grasp the implant for implantation. Specifically designed implantation instruments may be employed, particularly if the implant is made of a soft material and can be folded.

After the implant is passed through the incision, it is then positioned and centered on the anterior surface of the lens (specifically the anterior lens capsule) with care taken not to damage the underlying capsule. The implant is centered and positioned so that the peripheral aspect of the implant does not extend over or beyond the zonules to any significant degree as they insert onto the lens capsule peripherally. Prior to implantation, it is necessary to establish and maintain the anterior chamber with an air bubble, physiologic balanced salt solution or possibly with visco-elastic material (such as Healon, Occucoat or Viscoat), as is done in cataract surgery.

Once the epiphakic implant has been positioned on the anterior lens capsule and centered, it then remains to make the implant adherent to the underlying anterior lens capsule. This is accomplished as indicated above, by injection of the adhesive through a needle into the appropriate openings which are integral in the implant and designed to accept and direct the liquid adhesive material to the desired location. An alternative technique is that the adhesive may be injected directly between the implant and lens capsule to provide adhesion. The adhesive used in this manner (such as a cyanoacrylate type of glue) is in a liquid form and develops the adhesive bond after injection. The adhesive should be used as minimally as possible, and used primarily in the periphery to render the peripheral aspect of the implant adherent. The adhesive should not generally be used in the central optical axis area since it might interfere with the optics of the implant and the human eye lens.

A second type of adhesive may be employed as indicated above, this adhesive being a thermoplastic or thermosetting type of adhesive which becomes activated and develops its adhesive bond upon the application of energy, such as heat or light energy particularly. This type of adhesive is located, for the same reasons stated above, in the periphery of the implant, as an integral part of the implant design. The energy source is then directed and delivered to the site of the adhesive where the adhesive is activated and the adhesive bond between the epiphakic implant and the underlying anterior lens capsule is produced. Various sources of energy for adhesive activation may be employed. The laser is a particularly suitable energy source because of its ability to deliver a variable, well controlled, and intense amount of energy to a small and discrete area. Depending on the particular configuration of the laser delivery system, the energy may be directed and delivered from a source external to the eye (possibly mounted on and delivered through the operating microscope), or through an instrument tip introduced into the eye. In the case of the probe tip introduced into the eye for energy delivery, the tip may need to be placed directly in contact with, or possibly only in close proximity to the adhesive to be activated. That is to say, the tip may need to be directly physically in contact with the adhesive in order to deliver sufficient energy for bonding. The probe tip energy source may not need to come in contact with the implant or adhesive, in all cases, but may from actual contact with the implant and its adhesive. As mentioned, a possible and very suitable location for a laser source is attached to and working in conjunction with the operating microscope, which serves as its general guide for positioning. Activation of the laser or a probe tip is accomplished by a switch controlled by the operating surgeon.

Several spots or sites of adhesive bonding may be necessary to provide adequate adhesion and fixation of the implant to the underlying lens capsule. Therefore, several sites of energy application, or adhesive injection as the case may be, may be necessary around the peripheral aspect of the implant. These bonding locations at the periphery of the implant will be roughly circular or arcuate in shape, and basically will conform to the generally circular curvature of the implant periphery. As a general principle, the amount of adhesive used, the number of bonding sites employed, and the amount of bonding energy used (for example if a laser system is utilized) should all be kept to the minimum optimally necessary to accomplish satisfactory bonding and stable fixation. Also, as mentioned previously, it is desirable to avoid adhesive in the optical axis area of the eye if at all possible.

Once the sites of adhesive bonding are accomplished, and it is felt the implant is suitably and satisfactorily fixated, the incision is closed in the standard method using surgical suturing techniques common to cataract surgery. The anterior chamber is evacuated of the previously placed viscoelastic material or air bubble as is the surgeon's desire. The eye is then patched in the usual fashion common to the intraocular surgery. The procedure is then complete.

In another embodiment, the implant lens 21 may have a peripheral and surrounding edge or rim which is energy labile and upon being subjected to a localized energy source such as heat from an Argon laser beam, transforms itself into a glue like or adhesive material which then become adherent and bonds to the underlying human lens capsule.

Figure 11:
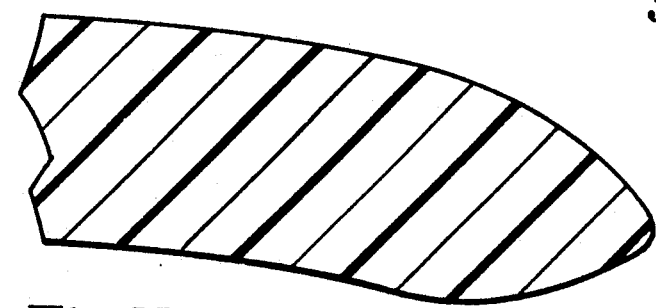
FIG. 11 is a partial cross-sectional view of a portion of an intraocular lens with a suboptimal edge profile with a thin peripheral edge but with the peripheral edge too anterior.
Figure 10:
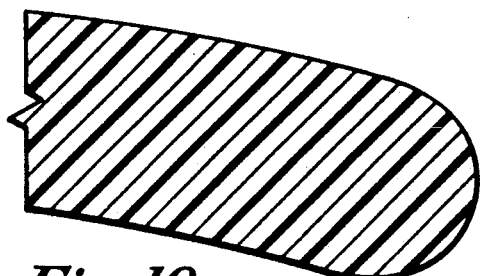
FIG. 10 is a partial cross-sectional view of a portion of an intraocular lens with a suboptimal edge profile with a rounded but thick peripheral edge.
Figure 12:
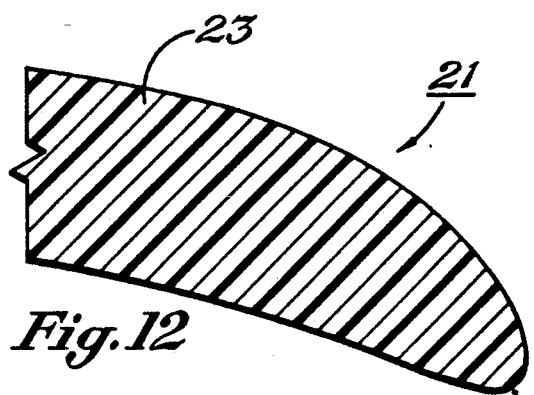
FIG. 12 is a partial cross-sectional view of a portion of an intraocular lens with the peripheral edge near the posterior surface and rounded.
Figure 13:
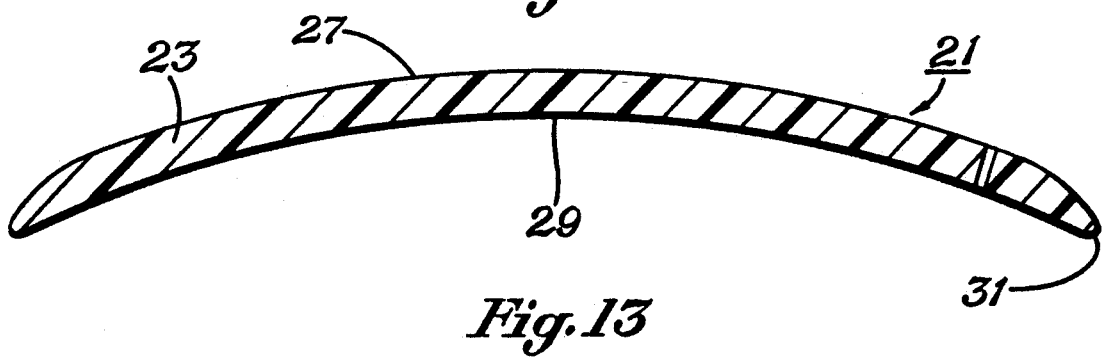
FIG. 13 is a cross-sectional view of an intraocular lens having an optimal edge profile with the peripheral edge posteriorly placed as in FIG. 12.

It is important to minimize physical contact between the intraocular implant lens 21 and the iris since it is known from clinical experience that similar contact between an intraocular lens implant and the iris can results in "chaffing" with resultant pigment dispersion, glaucoma, and iritis, with the ultimate result of generalized intolerance of the implant. Therefore, the periphery of the intraocular lens implant should be made as thin as possible to avoid excessive physical contact to the posterior surface of the iris which lies immediately anterior to the anterior surface of the implant lens. Producing thin peripheral edges may require the use of multiple different peripheral curvatures similar to techniques used in contact lens manufacturing. In addition to being as thin as possible, it is important that the peripheral edges be as smooth and rounded (non-sharp) to further minimize the trauma to any small amount of implant/iris physical contact that may exist. However, thinness, smoothness, and roundness are not the only aspects of peripheral edge design necessary for biocompatibility. Another feature is that in order to make the peripheral edge as minimally traumatic to the overlying iris as possible, it is necessary to locate the edge junction, that is the point of joining of the curves from the anterior and posterior implant surfaces, as far posteriorly as possible. FIG. 10 and 11 illustrate suboptimal edge profiles. In FIG. 10, the peripheral edge 31 is rounded but too thick. In FIG. 11, the peripheral edge 31 is thin but with the peripheral edge too anterior. FIGS. 12 and 13 illustrate optimal edge profiles. In these figures, the peripheral edge 31 of the intraocular lens 21 is located near the posterior surface and is rounded.

Figure 14:
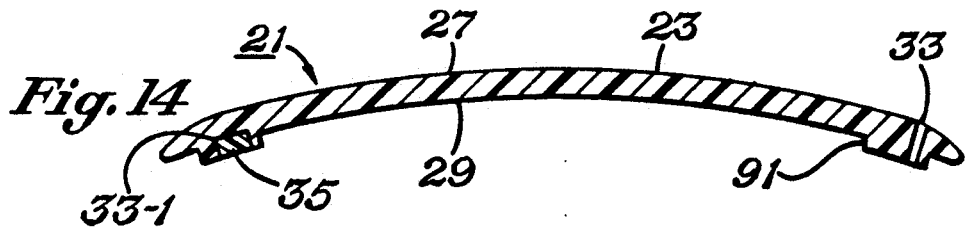
FIG. 14 is a cross sectional view of an artificial intraocular lens of another embodiment of the invention with "feet" extending from its posterior side.

In addition, the peripheral edge of the lens 21 may be designed with "feet" or structures to elevate the central body of the implant lens off of the capsule of the human lens to enhance nutrition of a human lens. In FIG. 14, such "feet" are illustrated at 91 and they comprise a plurality of separate, spaced apart members 91 extending from the posterior surface 29 of the lens 21 for engaging the anterior surface 43-1 of the human lens for seating the lens 21 against the human lens. The "feet" 91 may have dimensions radially such that small openings 33 may be formed completely through the "feet" from their posterior sides to the anterior side 27 of the lens 21 for receiving glue or adhesive for bonding the lens 21 to the human lens as disclosed and described in conjunction with FIGS. 1, 2, 4, and 5. As a further alternative, the openings 33-1 may be formed from the posterior side of the "feet" with the anterior side of the lens 21 covering the openings. Such openings may be filled with glue or adhesive 35 for bonding the lens 21 to the anterior surface of the eye as disclosed and described in conjunction with FIG. 3. Both of these alternatives are shown in FIG. 14, although it is to be understood that only one or the other may be used.

One purpose of the "feet" 91 is to allow the lens 21 to have different configurations such as plano-convex, rather than the concave-convex configuration of FIG. 1-7. In this respect, the lens 21 may employ a light convergent (plus) or light divergent (minus) configuration for the correction of hyperopia and myopia respectively. Modern technology may also make possible the development of multiple strength bifocal and multifocal optics for the correction of presbyopia either alone or in conjunction with the correction of hyperopia or myopia as is currently being investigated in the optics of intraocular implants used after the removal of a cataract. Also, the correction of astigmatism is at least theoretically, if not technologically possible.

In order to maintain sufficient nutrition to the human lens, nutrients contained in the aqueous humor, in particular, glucose, (but also oxygen, calcium and other substances) must have access to the anterior capsular surface of the human lens. This can be accomplished by use of the "feet" 91 which elevate the central body of the implant lens off of the surface of the capsule of the human lens by means of the peripheral feet or elevation structures 91. It is anticipated that this type of separation may be necessary if a material such as PMMA with its known low permeability is used in a substantial portion of the implant lens. Since the surface of the normal crystalline human lens is soft, the peripheral "feet" 91 may have to be relatively wide radially and also relatively long circumferentially to prevent the "feet" from sinking into depressions on the soft and pliable capsular surface of the human lens and hence to prevent any negating of the intended elevating effect of the "feet" 91.

Another method of increasing implant permeability is to provide the implant with perforations extending through the lens 21 between its anterior and posterior sides 27 and 29 at desired positions to allow for the passage of aqous through the implant such as has been accomplished in the previously mentioned polysulfone intracorneal implants being developed by Choyce. As an example, one perforation is shown at 24 in the lens of FIG. 13. It is important that central perforations (microperforations most likely), do not affect the optical performance of the implant lens.

Figure 16:
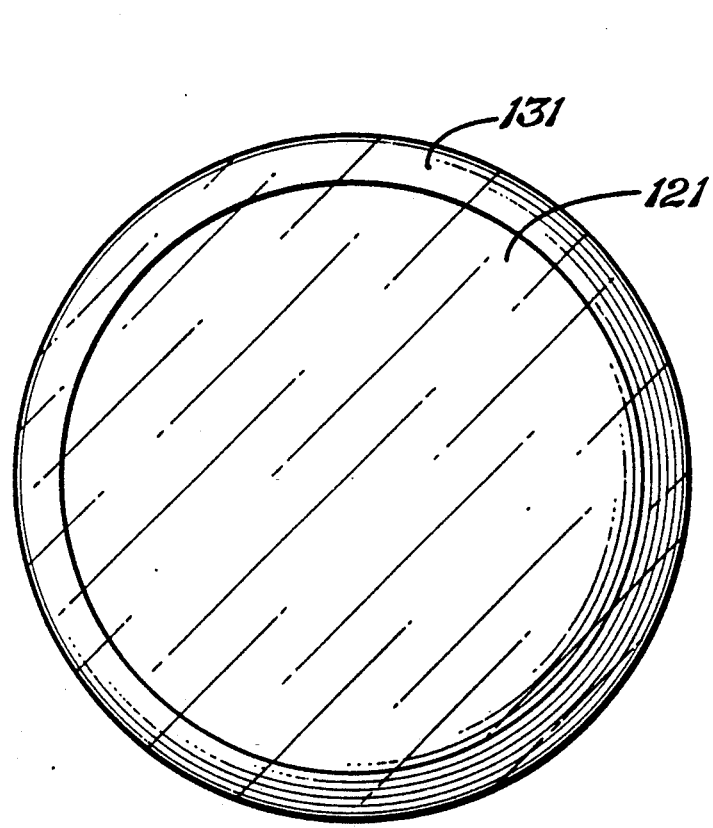
FIG. 16 is a plan view of an intraocular lens of another embodiment of the invention having a permeable central optical portion surrounded by and joined to an appropriate carrier ring.

In another embodiment, the implant lens may be formed from a material that is naturally permeable to the nutrient required by the human lens for normal metabolism. This may be accomplished by utilizing known gas permeable materials such as cellulose acetate, butyrate, siloxanyl/methacrylete combinations, silicone resins or hydrogels, etc., surrounded by a more energy resistant and resilient rim 131 such as shown in the embodiment of FIG. 16. In this embodiment, the permeable central optical portion 121 is surrounded by and joined to an appropriately thin carrier ring 131. The carrier ring 131 may have the openings 33 or 33-1 formed therethrough or therein for receiving the glue or adhesive for bonding purposes. Since the intraocular lens may be subjected to high energy levels, it is anticipated that the appropriate material for the implant lens be sufficiently energy resistant (thermo-resistant in the case of high energy heat application from a source such as Argon laser) to prevent degredation of the material. Again, this may require an implant design consisting of a central permeable optical element required for maintenance of human lens metabolism, joined to a more durable and energy resistant ring as shown in FIG. 16.

The overall shape of the implant lens preferably is generally circular to maximally fill the optical zone of the zonular free central lens surface. This has the advantage of maximally eliminating edge glare in the event of pupillary dilation in dim lighting conditions. The generally circular configuration, however, will have the theoretical disadvantage of covering the maximal surface area of the lens capsule thereby possibly producing the greatest alteration of normal lens metabolism. In order to avoid this problem, the shape of the intraocular lens, instead of being generally circular, may be elliptical, triangular, or square, or other shape as desired to maximally counterbalance the opposing concerns of edge glare and the maintenance of normal lens metabolism.

In considering the approach to proper fitting of the epiphakic implant to the anterior surface of the human lens, consideration must be given to both the convex curvature of the anterior capsular surface of the human lens and to the concave posterior curvature of the epiphakic implant. The fitting theories described by Kelman (U.S. Pat. No. 4,769,036) and Blackmore (U.S. Pat. No. 4,585,456) both consider an epiphakic implant with a posterior concave surface that is fit in direct contact with the convex anterior capsular surface of the human lens, particularly centrally.

With the epiphakic implant resting substantially on the center of the lens, the physical presence of the implant may impede the ability of the human lens to change its shape. Specifically, the physical presence of the implant resting on the convex anterior capsular curvature of the central portion of the human lens may prevent the anterior lens surface from bowing or curving forward as it naturally does during accommodation. It is a known physiologic fact that accommodation in the human lens is accomplished by the human lens changing its shape, particularly the shape of the anterior capsular surface of the lens. Even more specifically, the primary location of the change of the shape of the human lens, which accounts for a change in focus accompanying accommodation, is the central portion of the anterior capsule. The major configurational change occurs in the central capsular area because the central anterior capsule is thinner and therefore more pliable and capable of an alteration of configuration. Physiologic studies show that the change in lens power that is produced during accommodation is almost totally due to the change in configuration of the central part of the anterior capsule. It is known that the central anterior capsule bulges forward during accommodation producing the increased optical power in the lens. With the physical presence of a lens resting on the center of the anterior surface of the human lens, the ability of the lens capsule to change shapes may be significantly impeded, if not eliminated altogether, thereby diminishing or possibly eliminating the ability of the lens to change its focuses and thereby accommodate. It is this potential decrease or complete loss of accommodation that is the major disadvantage of fitting the implant in direct contact with the central area of the lens capsule.

Kelman (U.S. Pat. No. 4,769,085) describes his implant with "the posterior surface of the optic portion of such lens with a concave shape substantially conforming in curvature to the convex shape determined for the anterior surface of the natural lens of the eye when the latter is in is flattest natural condition".

The Kelman technique of fitting the implant to the anterior capsular surface when the capsule is in its flattest (unaccommodating) configuration greatly increases and compounds the problems of preserving accommodation because the implant is placed on the lens when it is least accommodating, thereby requiring the maximal configurational change in the lens to accomplish even the most modest amounts of accommodation. As mentioned, this anterior capsular forward bowing configurational change must be made directly against the unyielding physical presence of the implant which rests directly on the central capsule.

Figure 17:
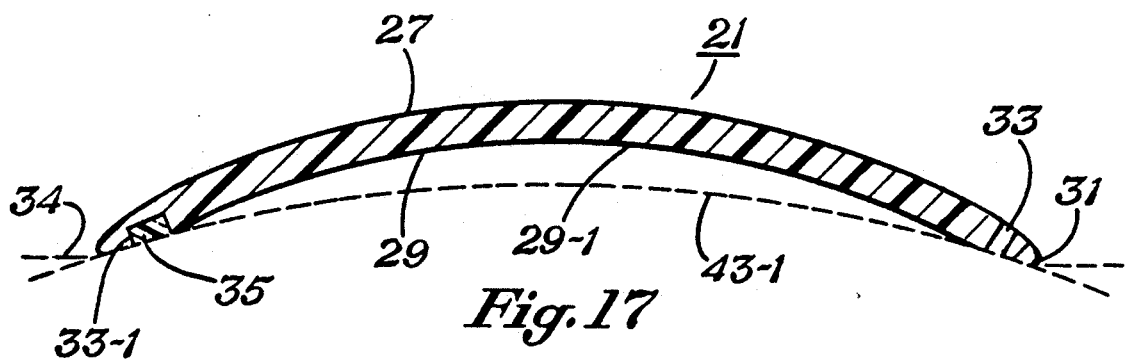
FIG. 17 is a cross-sectional view of another embodiment of the implant lens of the invention wherein the central portion of the posterior side of the lens is vaulted sufficiently to provide a space between this portion and the anterior capsular surface of the human lens.
Figure 18:
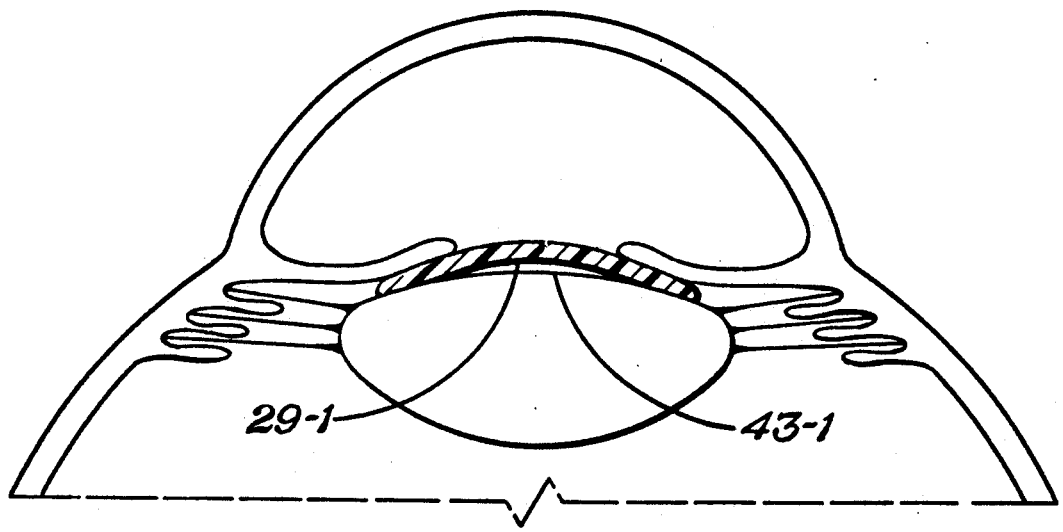
FIG. 18 illustrates the lens of FIG. 17 seated and glued against the anterior surface of the natural lens of the human eye.

With the above mentioned concern for the preservation of accommodation in mind, there is here provided a new and novel fitting theory and technique and epiphakic implant configuration in which the central aspect of the epiphakic implant is constructed so that the concave posterior curvature vaults above the central aspect of the human lens, thereby leaving a central space between the concave posterior curvature of the epiphakic implant and the convex anterior capsular surface of the human lens centrally. The periphery of the implant will still be in substantial contact with the convex anterior capsular surface, however, and the central portion is vaulted thereby leaving a small separation or space. Referring to FIGS. 17 and 18, the central portion 29-1 of the posterior side 29 of the lens 21 is vaulted from the plane 34 of its peripheral edge 31 sufficient that the central portion 29-1 of the posterior side 29 of the lens 21 will be spaced from the anterior capsular surface 43-1 of the human lens 43 when its periphery 31 seats against and engages the anterior capsular surface of the human lens. This fitting approach and epiphakic configuration has the advantage of allowing the human lens to change its shape naturally, thereby allowing and providing for natural accommodation. It also has the advantage of providing a space and compartment through which the aqueous humor may pass from between the bonding spots thereby providing access for essential nutrients from the aqueous humor to the anterior surface of the lens. Also, the change in configuration of the anterior surface of the human lens which occurs naturally with accommodation will at times shallow and then at other times deepen this small chamber space, thereby providing a "pumping" mechanism to move fluid in and out of the space. This also serves to enhance aqueous humor circulation across this area of the lens, which would otherwise be covered by the implant. It may be necessary to use peripheral holes in the implant to enhance and facilitate aqueous flow. It is anticipated that a space of approximately 0.5 mm (between the surface 29-1 of the lens 21 and the anterior capsular surface 43-1 of the human lens) will be sufficient to completely preserve accommodation, although a smaller or possibly a greater space may be necessary as will be determined from clinical experience.

Figure 15:
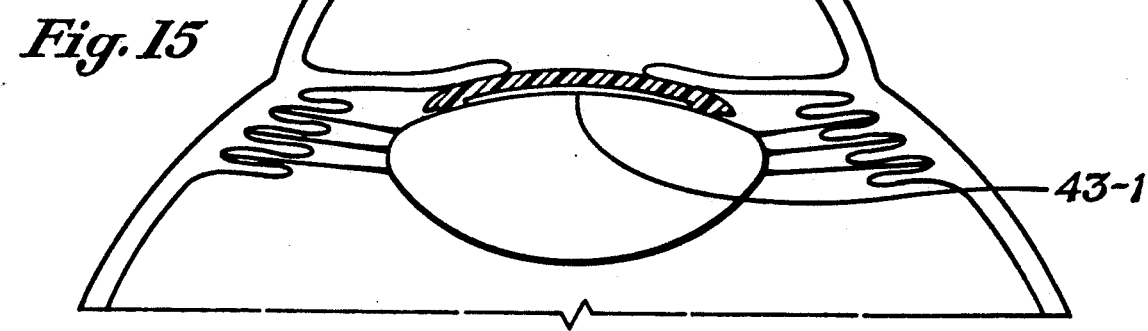
FIG. 15 is a partial cross-sectional view of the human eye the intraocular lens of FIG. 14 elevated off of the anterior surface of the human lens by the "feet" leaving a space between the intraocular lens and the human lens.
Figure 19:
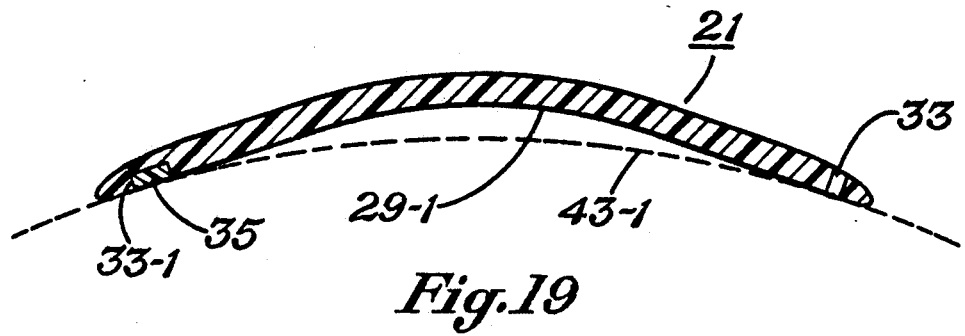
FIG. 19 is a cross-sectional view of an implant lens similar to that of FIGS. 17 and 18 but modified.

In the embodiment of FIGS. 17 and 18, the lens 21 near its peripheral edge 31, where it seats against the anterior surface of the human lens, may have the openings 33 or 33-1 formed therethrough or therein for receiving the glue or adhesive for bonding purposes as described previously. Both of these features are shown in FIG. 17, although it is to be understood that only one or the other may be used. The embodiment of FIGS. 17 and 18 has advantages over the embodiment of FIGS. 14 and 15 in that it provides more support and seating surface than the feet 91, thereby providing for more fixation surface and avoiding or minimizing sinking or depression of the lens implant into the soft capsular surface of the human lens. In the embodiment of FIG. 19, vaulting of the lens implant 21 at and near the edge is reduced and the angle of vaulting spaced inward from the edge toward the axis is greater in order to minimize contact of the lens with the iris.

Thus there is provided in the embodiment of FIGS. 17, 18, and 19 a new "vaulting" epiphakic implant fitting technique and configuration in which the posterior implant surface is rendered sufficiently concave to vault off the anterior surface of the human capsule, providing a space between the convex anterior capsular surface of the human lens and the concave posterior surface of the implant. This "vaulting" allows configurational changes to occur naturally in the central part of the anterior capsular surface or the human lens and thereby preserves natural accommodation of the human lens. The "vaulting" also provides superior access to the lens for the nutrient supplying aqueous humor.

Thus there is herein disclosed a new and unique type of refractive correction intraocular lens implant which is designed and intended for implantation upon and fixation to the anterior capsular surface of the human crystalline lens. Fixation is uniquely accomplished by direct adhesion to the anterior capsule of the human crystalline lens through the employment of glues or adhesive materials, or by the application of energy directly to the implant material itself, to produce implant-to-lens adhesions.

The overall dimensions of the implant lens are specifically and uniquely designed to be such that when the implant lens is positioned properly on the anterior surface of the human lens, its overall edge-to-edge dimensions are such that it remains central to or minimally overlapping the zonular attachments of the human crystalline lens. Furthermore, the implant lens periphery should be sufficiently thin, smooth, and rounded as to avoid an unacceptable amount of mechanical contact to the surrounding tissues, particularly the iris. In addition, the implant lens is constructed by design and materials to avoid substantially interfering with the normal metabolism of the human lens. The unique intraocular lens disclosed with its novel features of adhesive capsular fixation and physiologically appropriate dimensions, design, and materials is expected to result in an acceptably biocompatible and well tolerated refractive correction device for the human eye.

An intraocular lens implant is used to provide optical power within the eye which is lost after removal of a cataractous lens from the human eye. Generally, a particular desired overall refractive strength for the eye can be accomplished by making preoperative calculations using measurements determined from the corneal curvature and the axial length of the eye, and then based on these calculations, implanting a lens of a particular specified optical power which will then give the eye the desired overall optic power or refraction (myopic or hyperopic). It does happen occasionally, however, that the refractive power of the eye is found to be considerably different postoperatively from what was calculated, anticipated, and desired preoperatively. That is to say, the intended optical refractive result of the eye after removal of the cataract and implantation of the intraocular lens is considerably different from that expected and hoped for. This undesirable circumstance of postoperative refraction being considerably deviant from the desired refraction can be sufficiently extreme and intolerable as to require correction of the optical situation. This may be because of significant optical imbalance between the operated eye and the opposite eye, or simply because the optical correction is sufficiently strong as to be undesirable in and of itself. In fact, the presence of an undesirable optical result is one of the leading reasons for the need to replace a posterior chamber intraocular lens.

The only technique currently available for definitive correction of this undesirable optical condition is to remove the existing intraocular lens implant and replace it with an implant with a more proper optical power, which then results in restoration of the eye to the desired overall optical power and refraction. Removing the intraocular lens implant, however, can be an extremely difficult and traumatic operation to the eye and risks great damage to the eye in many cases. In fact, removing the intraocular lens can be sufficiently hazardous in some people such that it is avoided for fear of damage to the eye resulting in possible complete loss of vision and blindness. This is because, in order to remove an intraocular lens, especially a posterior chamber intraocular lens, it is necessary to free the implant from the adhesions that have developed around the implant, particularly around the haptic fixation members from the capsule, iris and ciliary body of the eye.

Because it is technically difficult and potentially dangerous to the eye to remove an existing intraocular lens, particularly a posterior chamber intraocular lens with associated adhesions, it is desirable to have a technique of changing the intraocular lens power without having to remove the existing intraocular lens. It is an object of the invention to provide such a means and process by use of an intraocular lens implant comprising essentially an optical portion which is placed within the eye directly on the optical portion of the already implanted intraocular lens. This process will eliminate the need to remove the already implanted intraocular lens.

The second implant which is placed directly on the optic of the already implanted intraocular lens will have an optical power such that its optical power, in combination with the already implanted intraocular lens, will combine to provide the overall desired optical power and refraction of the eye. This can be determined by using the known optical power of the eye with the implanted intraocular lens and creating the optical power of the second implant specifically for optical correction of the known optical deviation. Since this implant is placed directly on the optic of the already implanted intraocular lens it need not have any means of tissue fixation itself. It is simply placed directly upon the optic of the already implanted intraocular lens and made to fixate on the optic of the already implanted intraocular lens by one of several mechanisms including:

1. Adhesives.
2. Mechanical means including means for clipping around the optic edge or through existing optic holes of the previously implanted lens, should they be present.
3. Mechanical means for fixation around the haptic of the already existing implanted lens.

By this means of optically altering the overall power of the already implanted intraocular lens, the optical correction can be performed without requiring removal of the existing implant and avoiding technically difficult and potentially very damaging surgery which may otherwise be necessary to correct the situation. It can therefore be seen that this second implant placed on the optic of the already implanted intraocular lens will provide a means for optical power alteration and a safer process than exists at this time. It is also seen that in addition to simply correcting the optical power (by either making the eye more or less myopic or hyperopia), the second implant optic may contain bifocal or multifocal optics and thereby provide bifocal or multifocal capability to the already implanted intraocular lens which does not have multifocal (bifocal) capability. An additional need for optical change is to add the capability of bifocal or multifocal optic function to the already implanted intraocular lens, allowing the patient to minimize or completely eliminate the use of glasses. Correction may also be made for astigmatism.

This procedure can be performed on an already implanted intraocular lens in either the anterior chamber or the posterior chamber. Because generally relatively small amounts of optical power correction are required (relative to the overall optical power of the eye), the implant may be relatively thin compared to the optic of the already implanted intraocular lens. Because of its thin nature, if it is made of foldable materials, the implant may be folded or "rolled" and implanted through a very small incision. This will minimize surgical trauma even further. It is anticipated that this implant will be capable of fixation on the optic of the already implanted intraocular lens even if the anterior surface of the optic of the already implanted intraocular lens is partially covered by tissue such as anterior capsule peripherally.

Figures 20, 21:
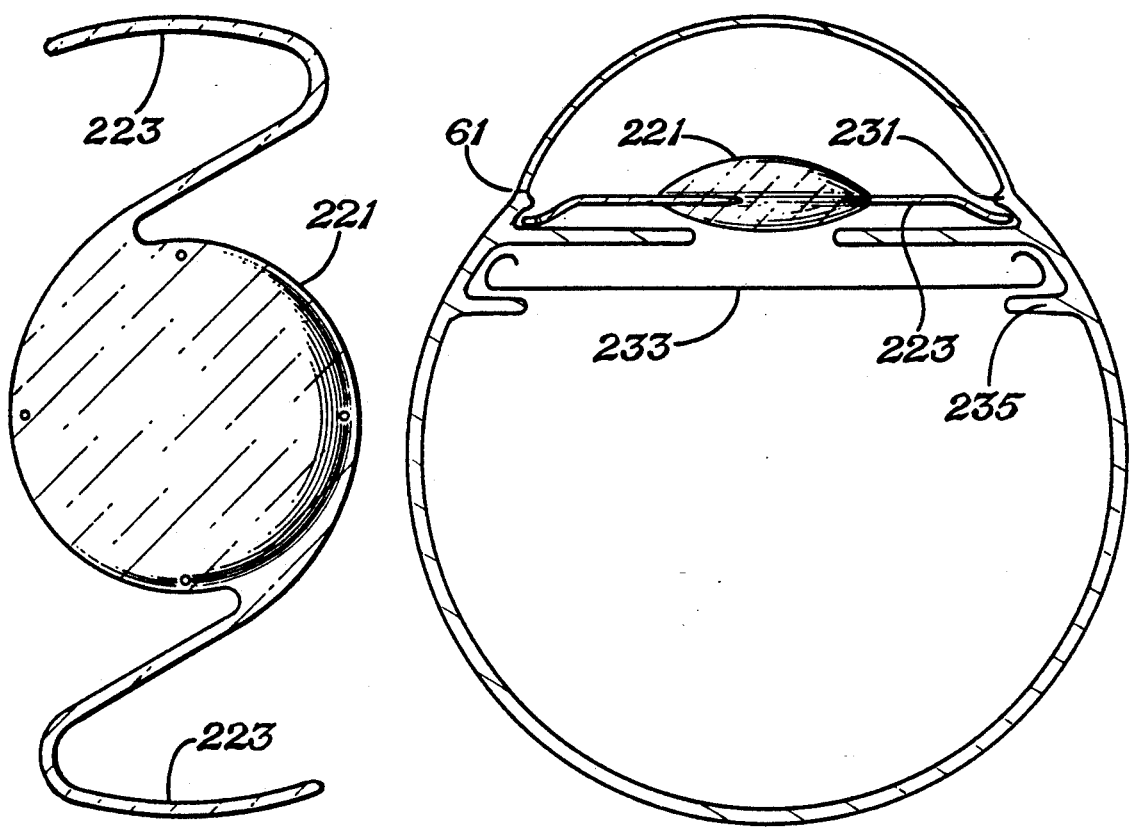
FIG. 20 is a plan view of an artificial intraocular lens with haptics similar to that described in U. S. Pat. No. 4,418,431.
FIG. 21 is a partial cross-sectional view of a human eye having the natural lens removed and the lens of FIG. 20 implanted in the anterior chamber.

Referring now to FIG. 20, there is disclosed an artificial intraocular lens comprising a transparent optic body 221 having two fixation loops or haptic members 223 extending outwardly from opposite sides of the periphery of the lens body 221. The fixation members 223 are identical in shape but are asymmetrically arranged relative to the lens body 221 for supporting the lens body in the eye as disclosed in U.S. Pat. No. 4,418,431 which is incorporated into this application by reference. FIG. 21 is a simplified partial cross-sectional view of any eye with the lens of FIG. 20 implanted in the anterior chamber. In FIG. 21, reference numeral 231 defines the seleral spur; 233 the posterior capsule; and 235 the ciliary body. In FIG. 21, the haptics 223 are seated in the area of the seleral spur such that the lens is implanted in the anterior chamber.

Figure 22:
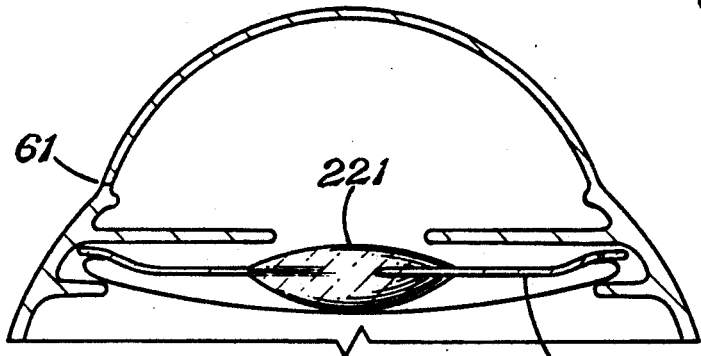
FIG. 22 is a partial cross-sectional view of a human eye having the natural lens removed and the lens of FIG. 20 implanted in the posterior chamber with its fixation members or haptics in the ciliary sulcus.
Figure 23:
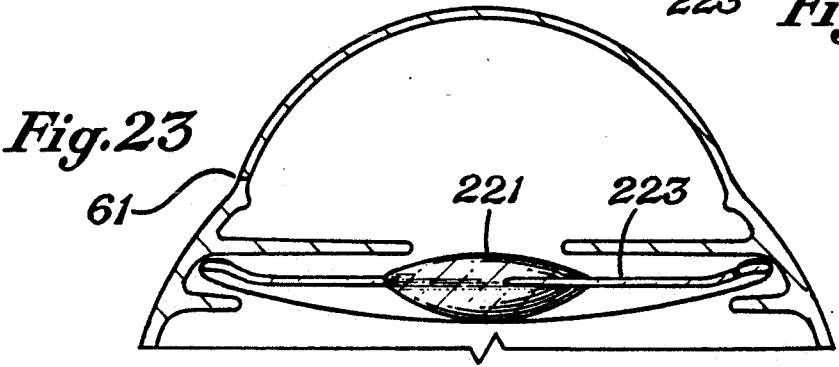
FIG. 23 is a partial cross-sectional view of a human eye having the natural lens removed and the lens of FIG. 20 implanted in the posterior chamber with its fixation members or haptics in the posterior capsular bag.

In FIG. 22, the lens of FIG. 20 is implanted in the posterior chamber with its fixation members 223 in the ciliary sulcus. In FIG. 23, the lens of FIG. 20 is implanted in the posterior chamber with its fixation members 223 in the posterior capsular bag. In FIGS. 20-23, the lens body is convex-convex.

Figure 24:
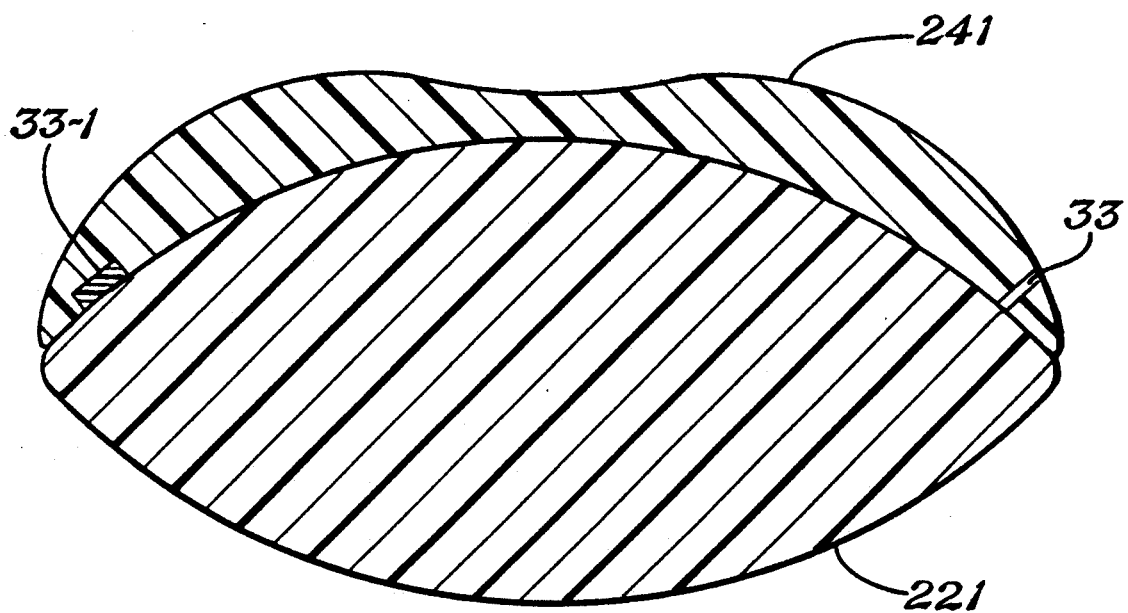
FIG. 24 is a cross-sectional view of an artificial intraocular lens seated on and attached to the anterior surface of the optic of a previously implanted artificial intraocular lens, and having curvature for myopic correction.
Figure 25:
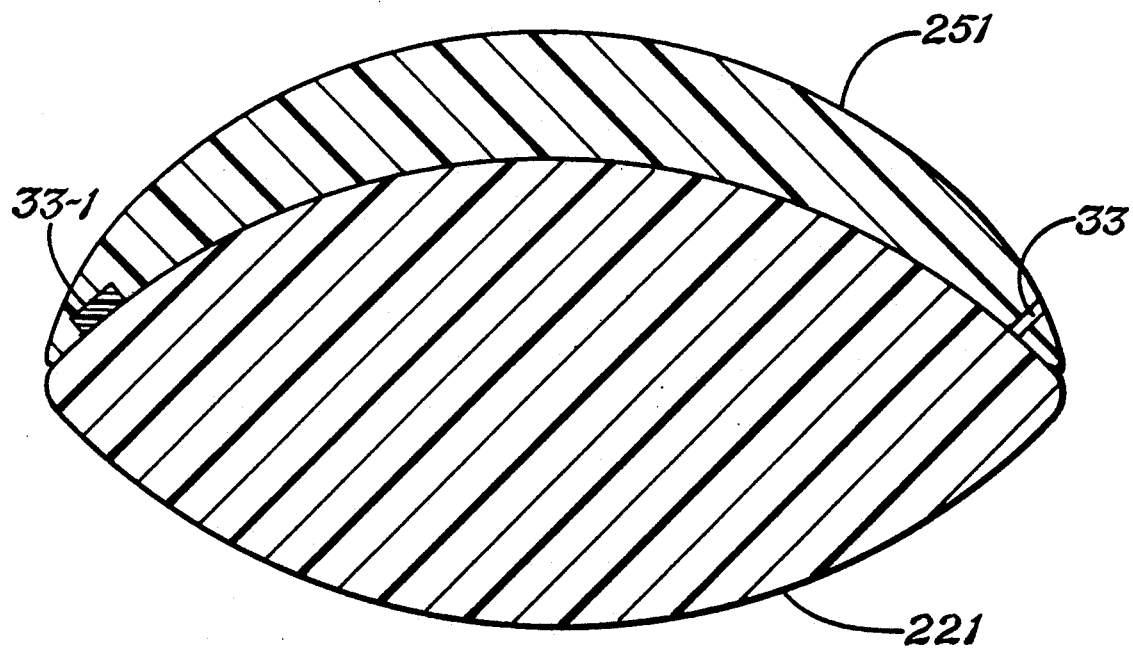
FIG. 25 is a cross-sectional view of an artificial intraocular lens seated on and attached to the anterior surface of the optic of a previously implanted artificial intraocular lens and having curvature for correction of hyperopia.
Figure 26:
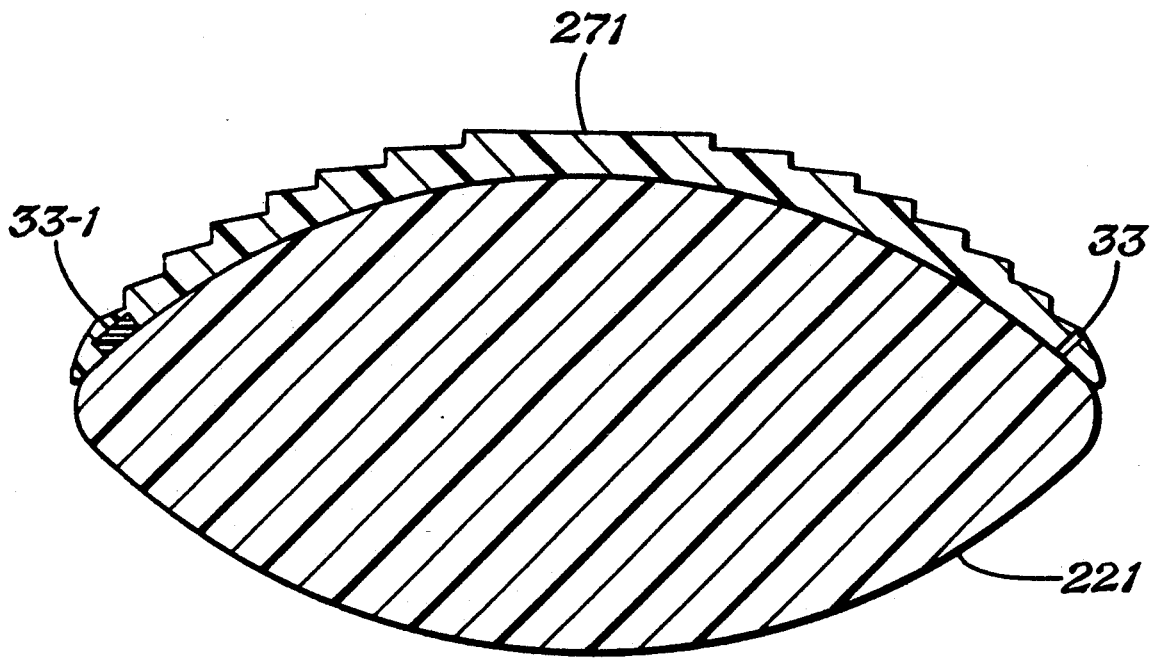
FIG. 26 is a cross-sectional view of an artificial intraocular lens having diffraction optics for bifocal or multifocal correction seated on and attached to the anterior surface of the optic of a previously implanted artificial intraocular lens. It is to be understood that the diffraction ridges could be located on the posterior side of the epiphakic implant.
Figure 27:
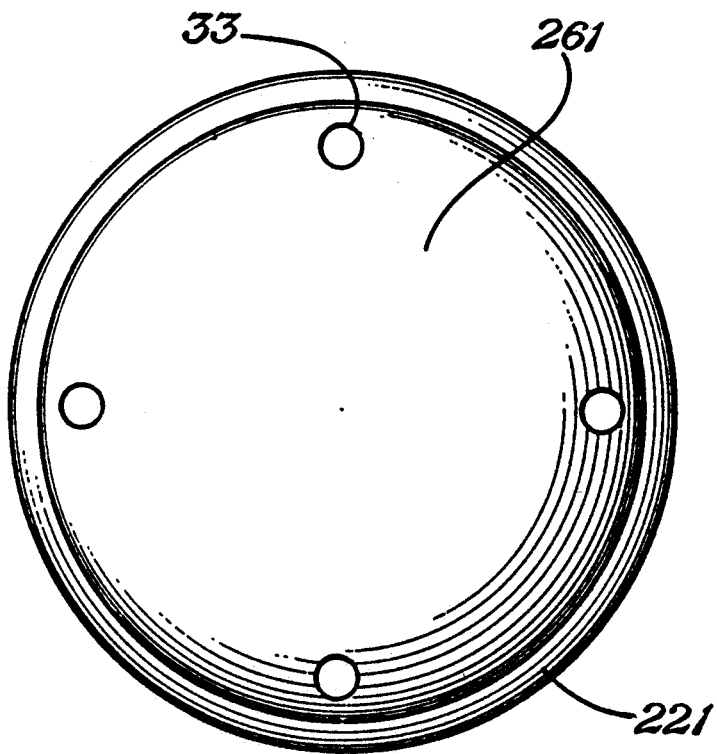
FIG. 27 is a plan view of an artificial intraocular lens seated on the optic of a previously implanted artificial intraocular lens.

The artificial intraocular lens previously implanted into the eye as disclosed for example in FIGS. 21, 22, and 23, can be optically altered and corrected by attaching a second intraocular lens to the anterior surface of the optic 221 of the implant either with glue or adhesive or with clips as now will be described. The operative procedure is the same as that disclosed above wherein an artificial intraocular lens was described as being inserted into the eye and seated on and attached to the anterior surface of the natural lens of the eye. In FIGS. 24-27, four artificial intraocular lenses 241, 251, 261 and 271 are shown as seated against and attached to the posterior surface of the optic 221 of the previously implanted lens with the use of wells 33 or 33-1 and glue or adhesive as described previously. If desired, a channel similar to channel 81 of FIGS. 6 and 7 may be formed on the posterior side of the lens 241, 251, and 271 of FIGS. 24-26 in communication with the aperture 33 to guide the adhesive. In the alternative, a tubular needle may be employed to inject the fluid adhesive between the periphery of the first and second implants without the use of the wells 33 or 33-1 as described above. The second implant may be formed of the same material as the first implant, that is PMMA as disclosed above, silicone materials, and virtually any material already used for intraocular lens implants. Referring to FIG. 24, the implant 241 has an anterior curvature for myopic correction. In FIG. 25, the lens 251 has an anterior curvature for correction of hyperopia. In FIG. 26, the lens implant 271 contains defraction optics on its anterior surface. In FIG. 27, the lens implant 261 has a diameter smaller than that of the previously implanted lens 221.

Figure 28:
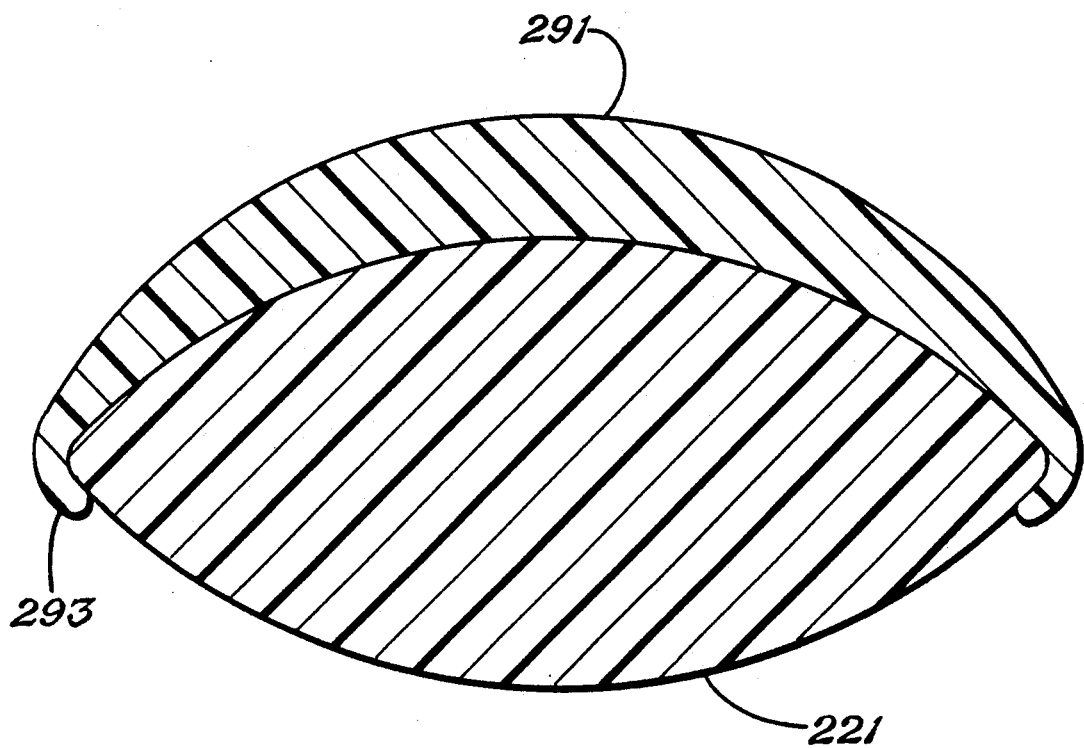
FIG. 28 is a cross-sectional view of an artificial intraocular lens seated on the anterior surface of the optic of a previously implanted artificial intraocular lens and having clips for holding the lens in place to the previously implanted lens.
Figure 29:
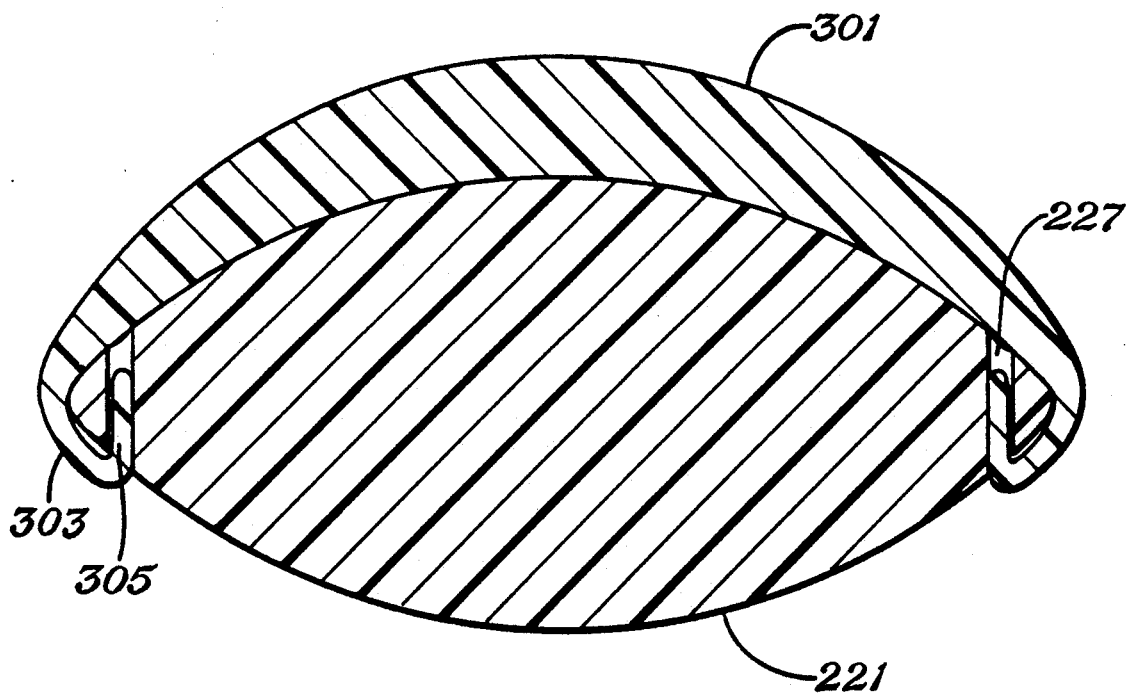
FIG. 29 is a cross-sectional view of an artificial intraocular lens seated on the anterior surface of the optic of a previously implanted artificial intraocular lens and having clips and pegs for holding the lens in place to the previously implanted lens.
Figure 30:
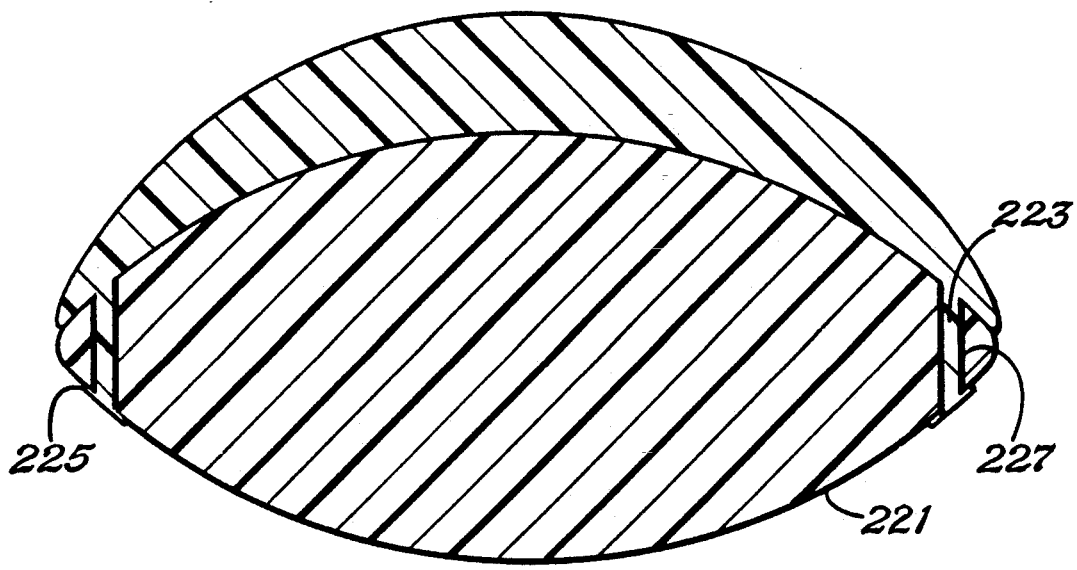
FIG. 30 is a cross-sectional view of artificial intraocular lens seated on the anterior surface of the optic of a previously implanted artificial intraocular lens and held in place by pegs and flanges extending through holes formed through the previously implanted lens.

Referring now the FIGS. 28, 29, and 30, there are disclosed intraocular lens implant members 291, 301, and 321 which employ spaced apart clips at their periphery for clipping the second implant to the first implant. The implants 291, 301, and 321 also may be formed of the same material that lenses 241, 251, 261, and 271 are formed as described above such as PMMA. In FIG. 28, the implant 291 has a plurality of spaced apart clipped clips 293 formed at its peripheral edge for clipping around the edge and onto the posterior surface of the implant 221. The clips 293 are resilient and can be sprung outward to allow the clips 293 to fit around the lens 221 and then released to allow the clips 293 to secure the lens 291 to the lens 221. In FIG. 29, the previously implanted lens 221 may have apertures 227 formed therethrough at selected positions as is common with intraocular implants lenses, for example as disclosed in U.S. Pat. No. 4,418,431, and the lens 301 has a plurality of spaced apart clip members 303 at its peripheral edge with pegs 305 which may be sprung outward for insertion about the edge of implant 221 and then released such that the pegs 305 enter the apertures 227 for holding the lens 301 to the lens 221. In FIG. 30, the lens 321 has a plurality of spaced apart peg members or rods 323 extending from its posterior side near its peripheral edge with resilient flanges 327. These peg members may be inserted through the apertures 227 with the flanges 327 moved backward against the peg members 323 and when the flanges are moved through the apertures 227 to the posterior side of the lens 221, they spring outward to hold the implant 321 against the implant 221. As an alternative the pegs 223 may be wedge shaped (with smaller free ends) and wedged into the apertures 227 for attaching the implant 321 to the implant 221. In addition, the pegs 223 may be formed of hardened adhesive for insertion into the apertures 227 and attached to the implant 221 with energy from a laser for attaching the implant 321 to the implant 221.

Figure 31:
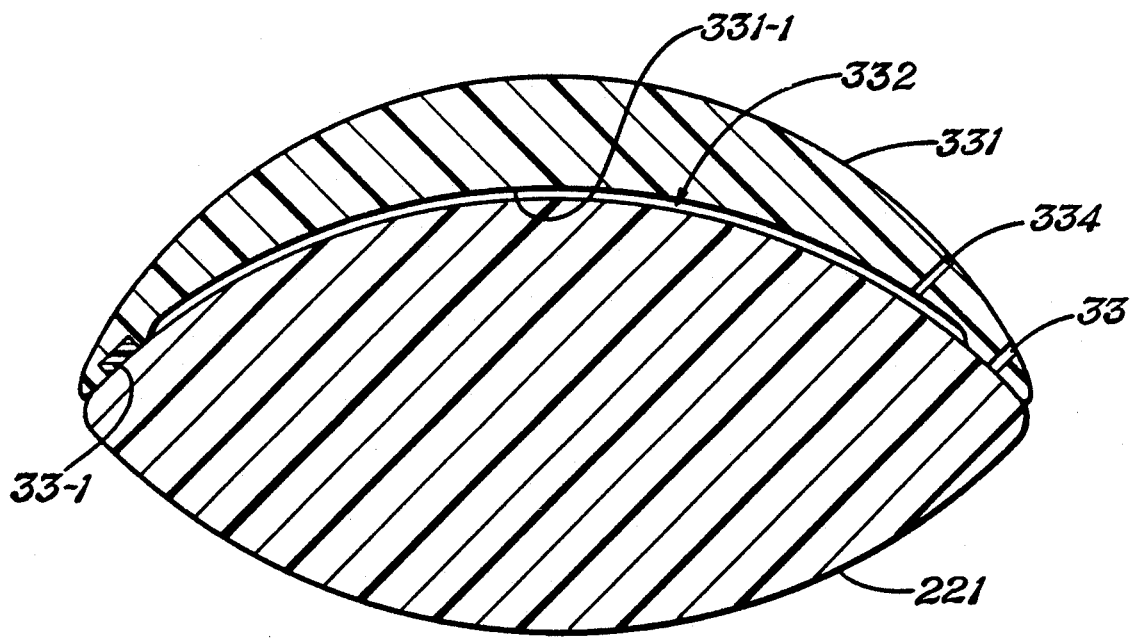
FIG. 31 is a cross-sectional view of an artificial intraocular lens resting peripherally on the optic of a previously implanted artificial intraocular lens with a central space between the two optics.

Referring to FIG. 31, the implant lens 331 may be formed of the same transparent material as described above, such as PMMA, however, its posterior surface 331-1 is formed such that there is a space 332 between the central portions of the posterior and anterior surfaces of the lenses 331 and 221 when the peripheral edge of the lens 381 engages and is seated against the peripheral edge of the implant 221 and attached in place for example, by adhesive using the wells 33 or 33-1 or injected by the use of a tubular needle between the two peripheral edges. The space 332 between the two optic members 231 and 221 will contain the aqueous of the eye eliminating the need for precise matching curvatures of the optic devices. Microperforations may be formed through the lens 331 near its peripheral edge, one of which is shown at 334 to allow for passage of the aqueous to the space 332.

Figure 32:
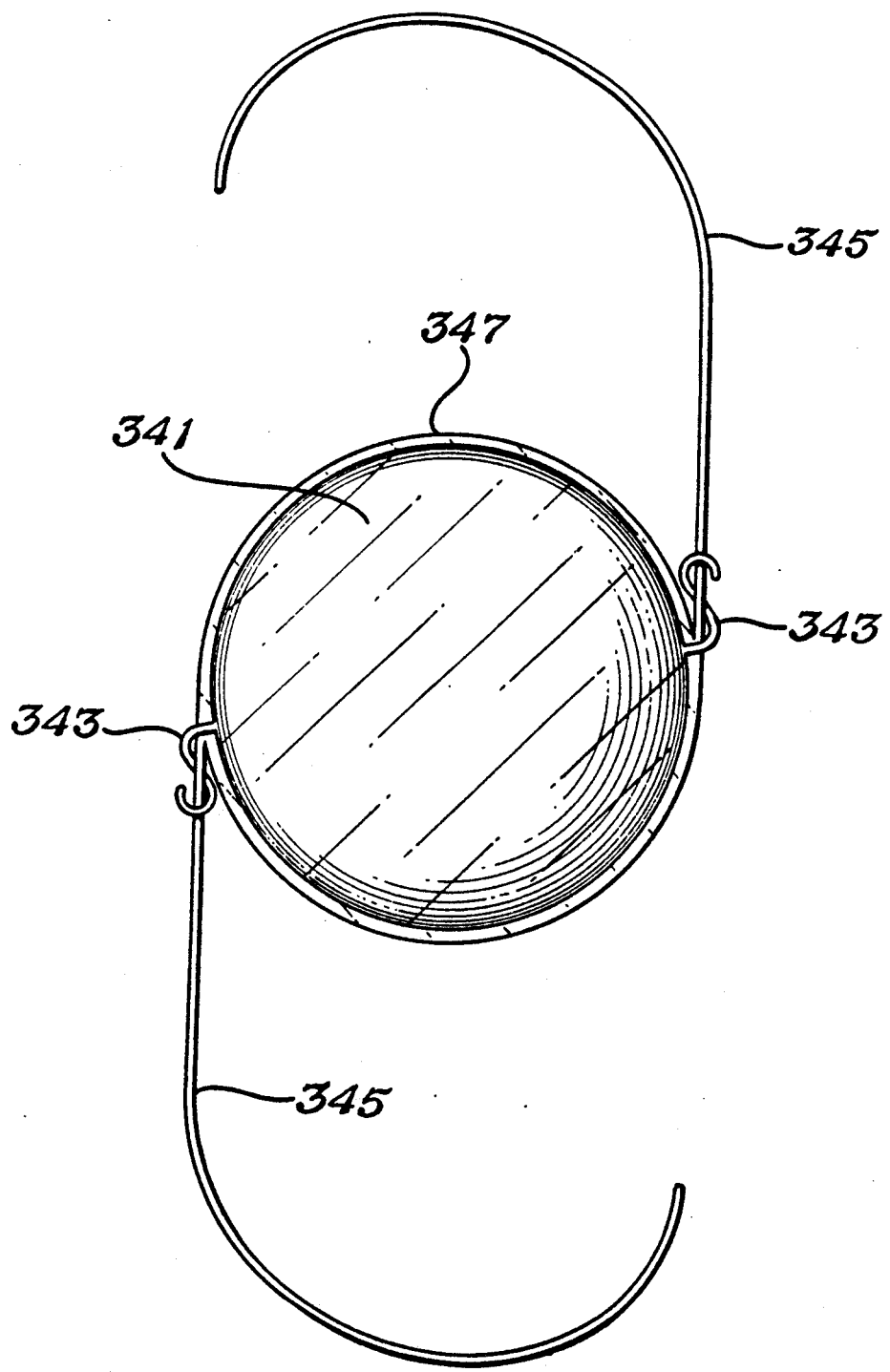
FIG. 32 illustrates an artificial intraocular lens attached by clips to the haptics of a previously implanted artificial intraocular lens.

FIG. 32 illustrates a transparent optic member 341 of an antificial intraocular lens having small resilient hooks or clips 343 extending from its peripheral edge which are hooked around the haptics 345 of an artificial intraocular lens 347 previously implanted in the eye to attach the optic member 341 to the optic member 347 with the posterior side of the optic member 341 facing and engaging the anterior side of the optic member 347. The lens 347 is implanted in the eye after the natural human lens is removed and is held in place in the eye by the haptics 345.

Although the second artificial lenses of FIGS. 24-31 were described as being attached to the previously implanted lens of the type shown in U.S. Pat. No. 4,418,431, it is to be understood that the second artificial lens of FIGS. 24-31 may be attached to previously implanted lenses having different optic body and haptic shapes.

As described above, the second implants of FIGS. 24-32 will be implanted through a limbal incision as is commonly used in cataract and intraocular lens surgery. The fixation surgical technique will vary depending on the particular fixation mechanism employed by the implant. The procedure will be performed in the usual sterile fashion for intraocular surgery in accordance with the principles of such surgery as described above with respect to the attachment of an artificial intraocular lens to the natural lens of the human eye.

Thus in the embodiments of FIGS. 24-32, as described above, there are provided artificial intraocular implants which have optical power which rests on the optic surface of an already implanted intraocular lens for optically changing the overall power of the previously implanted lens thereby correcting an existing undesirable optic situation. It is also seen that such second implants can have the ability to add bifocal function to the previously implanted intraocular lens which does not have bifocal function previously. It is seen that fixation of the second implant may be either by adhesive to the previously implanted optic surface or with "clip" means located around the optic edge; through existing optic holes; or around the adjacent haptics of the already implanted intraocular lens.

I claim:

1. A method of implanting an artificial intraocular lens into a human eye, comprising the steps of:

providing an artificial intraocular lens, forming an incision in the eye, inserting said artificial intraocular lens through said incision, into the eye, seating said artificial intraocular lens against the anterior surface of the natural lens of the eye in substantial optical alignment therewith, attaching said artificial intraocular lens to the anterior surface of the natural lens of the eye with an adhesive inserted into the eye through said incision, said artificial intraocular lens being attached to the anterior surface of the natural lens of the eye by attaching said adhesive to the anterior surface of the natural lens of the eye after said artificial intraocular lens is seated against the anterior surface of the natural lens of the eye in substantial optical alignment therewith.

2. The method of claim 1, wherein:

said artificial intraocular lens has opposite facing anterior and posterior sides with at least one aperture formed therethrough between said anterior and posterior sides, said adhesive is injected through said aperture to attach said artificial intraocular lens to the anterior surface of the natural lens of the eye.

3. The method of claim 1, wherein:

said artificial intraocular lens has opposite facing anterior and posterior sides with at least one well formed into said artificial intraocular lens at least from said posterior side, said well has said adhesive located therein when said artificial intraocular lens is inserted into the eye, said adhesive is attached to the anterior surface of the natural lens of the eye by applying energy to said adhesive when said artificial intraocular lens is seated against the anterior surface of the natural lens of the eye.

4. The method of claim 1, wherein:

said artificial intraocular lens has opposite facing anterior and posterior sides, said adhesive is injected between said posterior side of said artificial intraocular lens and the anterior surface of the natural lens of the eye by way of a hollow needle means to attach said artificial intraocular lens to the anterior surface of the natural lens of the eye.

5. The method of claim 1, wherein:

said artificial intraocular lens has an optical axis and anterior and posterior sides transverse to said optical axis and extending outward from said optical axis to a peripheral edge, said posterior side faces the anterior surface of the natural lens of the eye when said artificial intraocular lens is seated against the anterior surface of the natural lens of the eye, the maximum dimension of said artificial intraocular lens in a plane transverse to said optical axis being such that when said artificial intraocular lens is seated against the anterior surface of the natural lens of the eye in substantial optical alignment therewith, said artificial intraocular lens does not have any structure which extends beyond the peripheral edge of the natural lens of the eye.

6. A method of implanting an artificial intraocular lens into human eye, comprising the steps of:

providing an artificial intraocular lens, forming incision in the eye, inserting said artificial intraocular lens through said incision, into the eye, seating said artificial intraocular lens against the anterior surface of the natural lens of the eye in substantial optical alignment therewith, attaching said artificial intraocular lens to the anterior surface of the natural lens of the eye with an adhesive inserted into the eye through said incision such that said artificial intraocular lens is held in place in substantial optical alignment with the natural lens of the eye by said adhesive.

7. The method of claim 6, wherein:

said artificial intraocular lens has opposite facing anterior and posterior sides with at least one aperture formed therethrough between said anterior and posterior sides, said adhesive is injected through said aperture to attach said artificial intraocular 8. The method of claim 6, wherein:

said artificial intraocular lens has opposite facing anterior and posterior sides with at least one well formed into said artificial intraocular lens at least from said posterior side, said well has said adhesive located therein when said artificial intraocular lens is inserted into the eye, said adhesive is attached to the anterior surface of the natural lens of the eye by applying energy to said adhesive when said artificial intraocular lens is seated against the anterior surface of the natural lens of the eye.

9. The method of claim 6, wherein:

said artificial intraocular lens has opposite facing anterior and posterior sides, said adhesive is injected between said posterior side of said artificial intraocular lens and the anterior surface of the natural lens of the eye by way of a hollow needle means to attach said artificial intraocular lens to the anterior surface of the natural lens of the eye 10. The method of claim 6, wherein:

said artificial intraocular lens has an optical axis and anterior and posterior sides transverse to said optical axis and extending outward from said optical axis to a peripheral edge, said posterior side faces the anterior surface of the natural lens of the eye when said artificial intraocular lens is seated against the anterior surface of the natural lens of the eye, the maximum dimension of said artificial intraocular lens in a plane transverse to said optical axis being such that when said artificial intraocular lens is seated against the anterior surface of the natural lens of the eye in substantial optical alignment therewith, said artificial intraocular lens does not have any structure which extends beyond the peripheral edge of the natural lens of the eye.

11. An artificial intraocular lens for implantation in the eye of a human, comprising:

a transparent optic member having an optical axis and anterior and posterior sides transverse to said optical axis and extending outward from said optical axis to a peripheral edge, said transparent optic member being adapted to be inserted into the eye through an incision formed in the eye and seated against and attached to the anterior surface of the natural lens of the eye with its posterior side facing the anterior surface of the natural lens of the eye, the maximum dimension of said artificial intraocular lens in a plane transverse to said optical axis being such that when said artificial intraocular lens is seated against the anterior surface of the natural lens of the eye in substantial optical alignment therewith, said artificial intraocular lens does not have any structure which extends beyond the peripheral edge of the natural lens of the eye, and the central portion of said posterior side of said artificial intraocular lens near said axis is spaced from the plane of said peripheral edge of said artificial intraocular lens sufficient such that when said artificial intraocular lens is seated against the anterior surface of the natural lens of the eye, said posterior side of said artificial intraocular lens near said peripheral edge engages the anterior surface of the natural lens of the eye with said central portion of said posterior side of said artificial intraocular lens being spaced from the anterior surface of the natural lens of the eye.

12. The artificial intraocular lens of claim 11, comprising:

at least one aperture formed through said artificial intraocular lens near said peripheral edge and extending between said anterior and posterior sides of said artificial intraocular lens for receiving an adhesive for use for attaching said artificial intraocular lens to the anterior surface of the natural lens of the eye.

13. The artificial intraocular lens of claims 12, comprising:

a channel formed into said artificial intraocular lens from said posterior side and extending to said opening for guiding said adhesive when received through said opening.

14. The artificial intraocular lens of claims 11, comprising:

at least one opening formed into said artificial intraocular lens from said posterior side for receiving an adhesive for use for attaching said artificial intraocular lens to the anterior surface of the natural lens of the eye, said artificial intraocular lens comprising structure extending across said opening at one of said sides such that said opening does not extend through said artificial intraocular lens.

15. The artificial intraocular lens of claim 11, comprising:

support structure extending from said posterior side of said intraocular lens near its peripheral edge for engaging the anterior surface of the natural lens of the eye for maintaining said posterior side of said artificial intraocular lens spaced from the anterior surface of the natural lens of the eye.

16. The artificial intraocular lens of claims 11, comprising:

a surrounding rim attached to said peripheral edge of said transparent optic member and being formed of a material different from that of said transparent optic member, said transparent optic member being formed of a material permeable to the nutrients required by the natural lens of the eye for normal metabolism.

17. A method of implanting an artificial intraocular lens into a human eye, comprising the steps of:

providing an artificial intraocular lens, forming an incision in the eye, inserting said artificial intraocular lens through said incision, into the eye, seating said artificial intraocular lens against the anterior surface of the lens in the eye in substantial optical alignment therewith, and attaching said artificial intraocular lens to the anterior surface of the lens in the eye with an adhesive inserted into the eye through said incision.

18. The method of claim 17, wherein:

said lens in the eye is the natural lens of the human and said artificial intraocular lens is seated against and attached to the natural lens in the eye with said adhesive.

19. The method of claim 17, wherein:

said lens in the eye is an artificial intraocular lens previously implanted into the eye, said artificial intraocular lens inserted through said incision is seated against and attached with said adhesive to said artificial intraocular lens previously implanted in the eye.

20. A method of implanting an artificial intraocular lens into a human eye, comprising the steps of:

providing an artificial intraocular lens, forming an incision in the eye, inserting said artificial intraocular lens through said incision, into the eye, seating said artificial intraocular lens against the anterior surface of the lens in the eye in substantial optical alignment therewith, and permanently bonding said artificial intraocular lens to the anterior surface of the lens in the eye.

21. The method of claim 20, wherein:

said articulate intraocular lens is permanently bonded to the lens in the eye with an adhesive type material.

22. The method of claim 20, wherein:

said lens in the eye is the natural lens of the human and said artificial intraocular lens is seated against and permanently bonded to the natural lens in the eye.

23. A method of implanting an artificial intraocular lens into a human eye, comprising the steps of:

providing a artificial intraocular lens, forming an incision in the eye, inserting said artificial intraocular lens through said incision, into the eye, seating said artificial intraocular lens against the anterior surface of the lens in the eye in substantial optical alignment therewith, and attaching said artificial intraocular lens to the anterior surface of the lens in the eye with the use of laser energy applied into the eye from an external source of laser energy.

24. The method of claim 22, wherein:
said artificial intraocular lens is attached to the anterior surface of the lens in the eye with the use of said laser energy and an adhesive type material.

25. The method of claim 23, wherein:
said lens in the eye is the natural lens of the human and said artificial intraocular lens is seated against and attached to the natural lens in the eye.

* * * * *